(12) United States Patent
Wong et al.

(10) Patent No.: US 8,105,636 B2
(45) Date of Patent: Jan. 31, 2012

(54) COMPOSITIONS AND METHODS FOR TREATING INFLAMMATION AND INFLAMMATION-RELATED DISORDERS BY *PLECTRANTHUS AMBOINICUS* EXTRACTS

(75) Inventors: Chi-Huey Wong, La Jolla, CA (US); Yih-Shyun E. Cheng, Taipei (TW); Hui-Ming Yu, Sijhih (TW); Ting-Jen R. Cheng, Taipei (TW); Chung-Yi Wu, Nankang (TW); Jim-Min Fang, Taipei (TW)

(73) Assignee: Academia Sinica, Nankang (TW)

( * ) Notice: Subject to any disclaimer, the term of this patent is extended or adjusted under 35 U.S.C. 154(b) by 436 days.

(21) Appl. No.: 12/212,607

(22) Filed: Sep. 17, 2008

(65) Prior Publication Data

US 2009/0076143 A1    Mar. 19, 2009

Related U.S. Application Data

(60) Provisional application No. 60/973,164, filed on Sep. 17, 2007.

(51) Int. Cl.
*A61K 36/00* (2006.01)
*A61K 31/045* (2006.01)
*A61K 31/05* (2006.01)

(52) U.S. Cl. .................. 424/725; 514/729; 514/732

(58) Field of Classification Search .................. None
See application file for complete search history.

(56) References Cited

U.S. PATENT DOCUMENTS

| 2004/0146593 | A1 | 7/2004 | Han et al. | |
|---|---|---|---|---|
| 2006/0099283 | A1 | 5/2006 | Wei et al. | |
| 2007/0237841 | A1 * | 10/2007 | Wu et al. | 424/725 |
| 2008/0069911 | A1 * | 3/2008 | Wu et al. | 424/745 |

FOREIGN PATENT DOCUMENTS

| IN | 200400002 | * | 4/2006 |
|---|---|---|---|
| KR | 10-2002-88211 A | | 11/2002 |
| WO | WO 02/094301 A1 | | 11/2002 |

OTHER PUBLICATIONS

M. Abdel-Mogib et al, Chemistry of the Genus *Plectranthus*, Molecules 2002, 7(2), 271-301.
Heather A. Ferguson et al, Expression and purification of recombinant human c-Fos/c-Jun that is highly active in DNA binding and transcriptional activation in vitro, Nucleic Acids Research, 2001, vol. 29, No. 20 e98.
K. Terpe, Overview of tag protein fusions: from molecular and biochemical fundamentals to commercial systems, Appl Microbiol Biotechnol (2003) 60:523-533.
International Search Report.

* cited by examiner

*Primary Examiner* — Christopher R. Tate
(74) *Attorney, Agent, or Firm* — Occhiuti Rohlicek & Tsao LLP

(57) ABSTRACT

The crude extract of *Plectranthus Amboinicus* (PA) has anti-inflammatory effects and can inhibit AP-1 binding in vitro. The incubation with PA crude extract resulted in significant inhibition of the LPS-induced expression of IL-6, IL-12, MCP-1, and RANTES in HUVEC cells. After the crude extract was further fractionated using preparative HPLC, fraction 8, 9, 10 and 11 were identified to inhibit the AP-1 binding activity. The active component of fraction 8 is Mena 987; fraction 9 is Mena 998; fraction 10 is Mena 9102; and fraction 11 is rosmarinic acid and the synthetic rosmarinic acid analogues. Other compounds showed inhibitory activities as well. These compounds have inhibitory effects on AP-1 activity and are useful as preventive or therapeutic agent for diseases in which excessive expression or activities of AP-1 are involved.

2 Claims, 16 Drawing Sheets

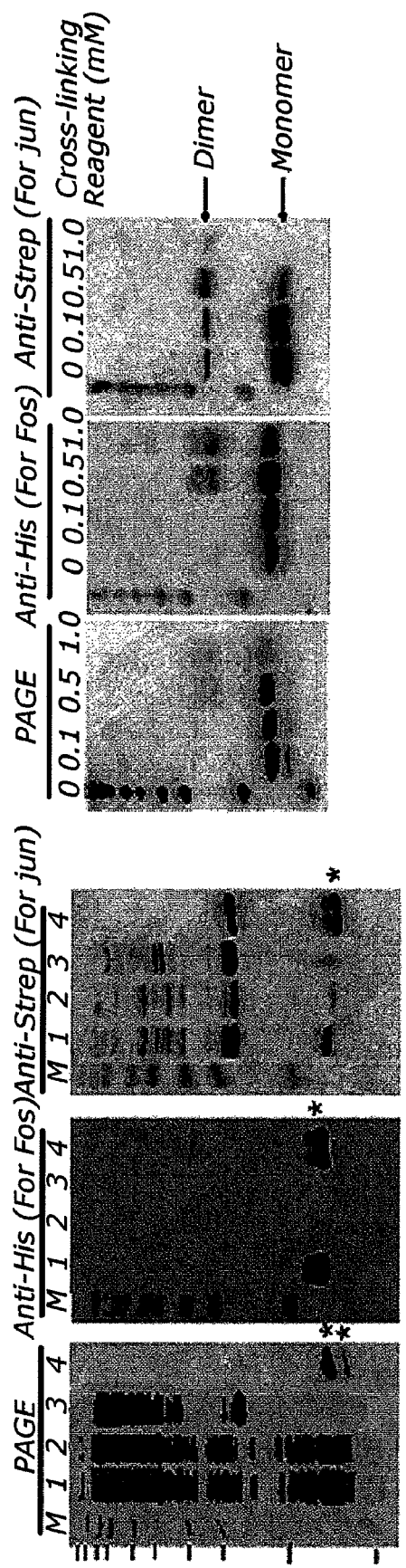
FIG. 8A
FIG. 8B
FIG. 8C

COMPOSITIONS AND METHODS FOR TREATING INFLAMMATION AND INFLAMMATION-RELATED DISORDERS BY *PLECTRANTHUS AMBOINICUS* EXTRACTS

RELATED APPLICATION

The present disclosure incorporates by reference and claims the Paris Convention Priority of U.S. Provisional Application No. 60/973,164, filed Sep. 17, 2007.

BACKGROUND

*Plectranthus amboinicus* (PA) is a traditional Chinese medicine used for coughs, sore throats, and nasal congestion, but also for a range of other problems such as infections, rheumatism, and flatulence. Although the chemical constituents of PA have been extensively studied, its active ingredients for inhibition of AP-1 binding have not been reported.

The transcription factor activator protein-1 (AP-1) regulates expression of various genes by binding to a consensus DNA recognition sequence TGA(C/G)TCA also known as a TPA responsive element (TRE) in the promoter region of target genes. In mammalian cells, AP-1 complexes are mainly formed by members of Fos and Jun-related proteins. AP-1 proteins contain a characteristic amino acid sequence called the bZIP domain. This domain is bipartite; it contains helical conformation and serves as a dimerization interfaces. Interactions between two leucine repeats juxtapose the N-terminal basic regions of two bZIP domains to form a DNA-binding-competent dimer. In vitro studies indicated that stable heterodimer can form between one member of the Fos family and one of Jun class. Jun homodimer can be formed in vitro; yet they are unstable in physiological conditions. Fos homodimer has not been found in normal experimental conditions. In vitro binding and transcription studies indicate that Fos-Jun heterodimer is the predominant active species of AP-1 proteins.

AP-1 activation followed by increased expression of certain genes is a regulator of final steps in a wide range of cellular processes, such as inflammation, stress response, cell differentiation, and tumorigenesis. Therefore, inhibiting the formation of the AP-1-DNA complex is an approach for reducing inflammation and cancer progression. AP-1 activities have been implicated in several autoimmune diseases such as colitis, lupus erythematosus, and rheumatoid arthritis.

Generally, inflammation signaling pathways leads to the activation of several transcription factors including AP-1, which then activate immune cells and induce differentiation of specific cells. A markedly increased expression and high DNA binding activity of AP-1 is found in rheumatoid arthritis synovium. In addition, overexpression of c-fos caused overgrowth of synovial cells and arthritic joint destruction. These observations have led to hypothesize that modulating DNA binding activities of AP-1 may reduce the progression of inflammation in diseases. In fact, the administration of decoy AP-1 oligonucleotides has been shown to reduce collagen-induced arthritis and to attenuate intenstinal inflammation in murine experimental colitis.

Based on these observations, efforts have been made in development of AP-1 inhibitors for inflammatory diseases and cancer. Curcumin, a powerful inhibitor of AP-1 binding activities, has been shown to have anti-cancer activities and can suppress osteoclastogenesis and stimulate osteoclast apoptosis. Momordin I, a strong inhibitor for Jun/Fos dimer formation and the AP-1-DNA binding, can inhibit cancer cell proliferation by inducing apoptosis.

Inflammation has a broad spectrum involvement in many human acute and chronic diseases including allergies, arthritis, gingivitis and most of "-itis" diseases. Inflammation usually starts with tissue injury and subsequent attraction of immune cells to the injured regions to promote healing. Inflammation protects the body, however, it also damages the body if the inflammatory response is unbalanced and outweighs the threat it is dealing with. The anti-inflammatory drugs can be potentially used for autoimmune diseases, rheumatoid arthritis (RA), allergy, cancer, heart disease, and arthrosclerosis. RA is an inflammatory disease mediated by enhanced T-cell activity and is characterized by synovitis and erosion of periarticular bone and joint destruction due to excessive subchondral osteoclastic resorption. Therapeutic management of RA has focused on the development of anti-inflammatory drugs that block cytokine signaling. Current treatments are NSAIDs (nonsteroidal anti-inflammatory drugs), corticosteroids, and DMARDs (Disease Modifying Antirheumatoid Drugs) such as methotrexate, TNF inhibitors, and Actemra (tocilizumab), a humanized anti-human interleukin-6 (IL-6) receptor monoclonal antibody.

Inflammation is a response of a tissue to injury. It attracts immune cells for healing via regulation of a variety of different cytokines, which are predominantly activated by the transcription factors of the NF-κB, AP-1, and NFAT, and STAT families. Activator protein-1 (AP-1) is a transcriptional factor that is activated during the cell cycle to promote cell survival, differentiation and adaptive responses. It was recently shown that AP-1 activity is involved in inflammation signaling, suggesting AP-1 may be a new target to intervene inflammation-related diseases.

SUMMARY

The crude extract of *Plectranthus Amboinicus* (PA) has anti-inflammatory effects and can inhibit AP-1 binding in vitro. The incubation with PA crude extract resulted in significant inhibition of the LPS-induced expression of IL-6, IL-12, MCP-1, and RANTES in HUVEC cells. After the crude extract was further fractionated using preparative HPLC, fraction 8, 9, 10 and 11 were identified to inhibit the AP-1 binding activity. The active component of fraction 8 is Mena 987; fraction 9 is Mena 998; fraction 10 is Mena 9102; and fraction 11 is rosmarinic acid and the synthetic rosmarinic acid analogues. Other compounds showed inhibitory activities as well. These compounds have inhibitory effects on AP-1 activity and are useful as preventive or therapeutic agent for diseases in which excessive expression or activities of AP-1 are involved.

According to features of the present disclosure, a composition is disclosed comprising an extract of *Plectranthus amboinicus* and a pharmaceutically acceptable carrier.

According to features of the present disclosure, a method is disclosed comprising providing a composition containing at least a *Plectranthus amboinicus* extract and a pharmaceutically acceptable carrier for administration in a therapeutically effective amount to a patient in need thereof.

According to features of the present disclosure, a method is disclosed comprising preparing a recombinant Fos-Jun complex, wherein the Fos-Jun complex is produced from a vector having a Fos gene and a Jun gene, and a first tag gene associated with the Fos gene and a second tag gene associated with the His gene, wherein the first tag gene is different from the second tag gene; screening for the Fos-Jun complexes by performing a first screening of the gene products of the vector with one tag to produce a partially screened gene product set; and screening the partially screened gene product set with the other tag to isolate the Fos-Jun complexes.

A method is disclosed for treating inflammation or an inflammation-related disorder. The method comprises the steps of providing a composition containing at least *Plectran-* thus amboinicus extract and administering a therapeutically effective amount of the composition to a patient in need thereof.

In another aspect of the present disclosure, a method is disclosed for treating inflammation or an inflammation-related disorder. The method comprises the steps of providing a composition comprising a compound of the general structure:

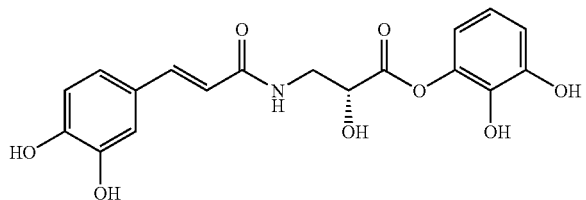

and administering a therapeutically effective amount of the composition to a patient in need thereof.

A composition for treating inflammation or an inflammation-related disorder is disclosed. The composition comprises a *Plectranthus amboinicus* extract.

In another aspect of the present disclosure, a composition for treating inflammation or an inflammation-related disorder is disclosed. The composition comprises a compound of the general structure:

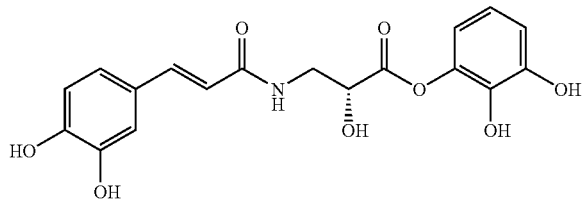

This present disclosure relates to an extract of *Plectranthus amboinicus* (PA), its active ingredients (rosmarinic acid, Mena 987, Mena 998, Mena 9102), the synthetic rosmarinic acid analogues and their use for AP-1 inhibition, for treating inflammation-related diseases.

In one aspect, the extract of *Plectranthus amboinicus* (PA) showed inhibition activities of AP-1 complexes. These AP-1 complexes can be formed, but not limited, by C-Jun, JunB, JunD, c-Fos, Fos-B, Fra-1 or Fra-2.

In one aspect, the present disclosure features an extract of *Plectranthus amboinicus*. The extract contains (or consist essentially of) 0.5-1.2% by weight rosmarinic acid, 0.05-0.1% by weight Mena 987, 0.05-0.1% by weight Mena 998, and 0.05-0.1% by weight Mena 9102. In particular, the extract may include (or consist essentially of) 0.89% by weight rosmarinic acid, 0.06% by weight Mena 987, 0.09% by weight Mena 998, and 0.08% by weight Mena 9102. The extract may contain (or consist essentially of) at least 30% by weight polyphenols.

The *Plectranthus amboinicus* extract of the present disclosure can be produced, e.g. by $RPC_{18}$-HPLC purification of dried *Plectranthus amboinicus* leaf juice powder and used G13658 UV/VIS detector, all the samples were monitored at 214 nm. The method of producing the P.A. extract is within the present disclosure.

The present disclosure also features a method for the AP-1 inhibition assay to evaluate the activities of the *Plectranthus amboinicus* extract ingredients.

DRAWINGS

The above-mentioned features and objects of the present disclosure will become more apparent with reference to the following description taken in conjunction with the accompanying drawings wherein like reference numerals denote like elements and in which:

FIG. 8 are experimental results of an implementation of experimental data showing a single-step purification of recombinant Fos-Jun complexes from bacterial cells;

DETAILED DESCRIPTION

Figure 1:
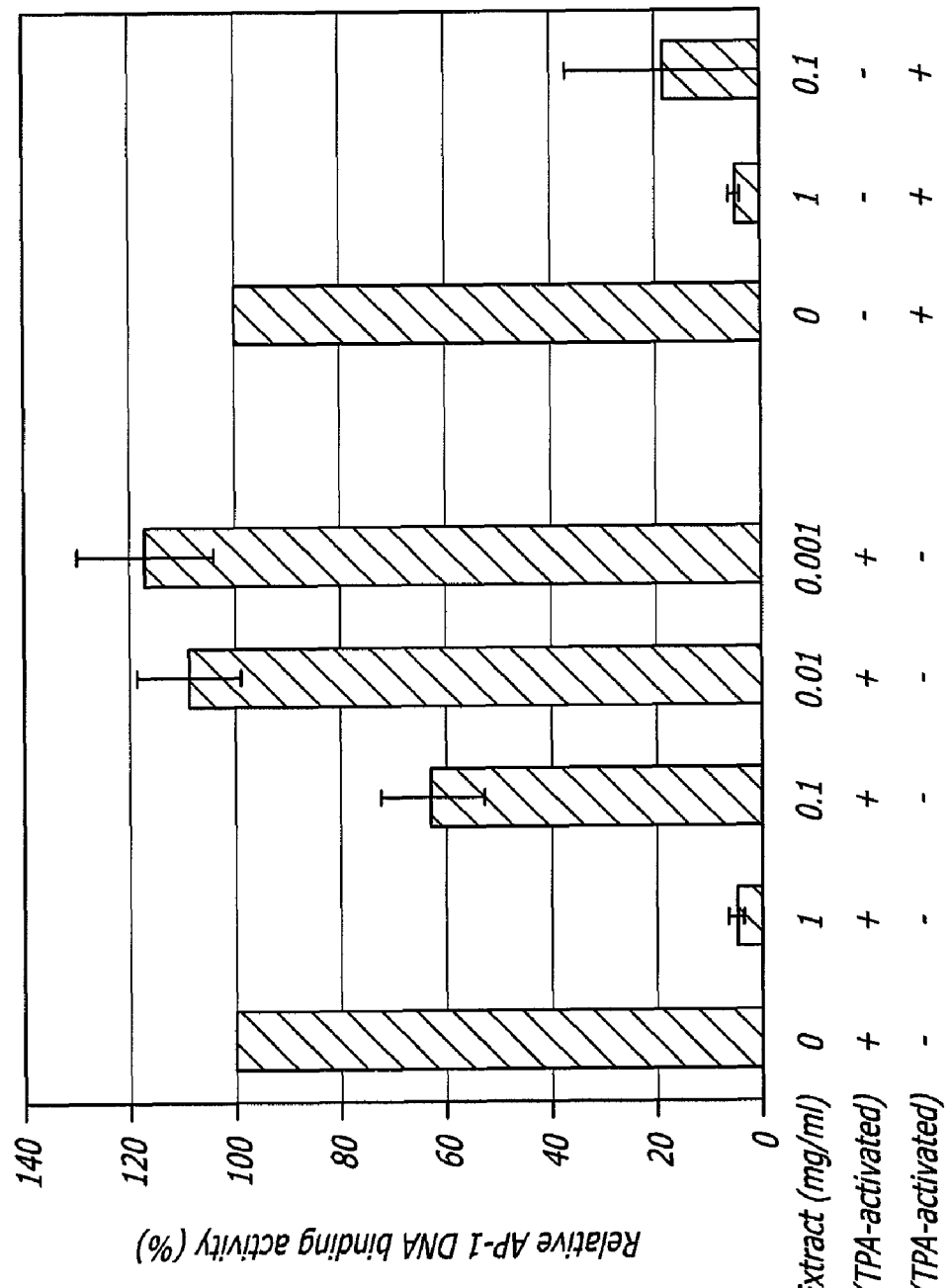
FIG. 1 is a bar graph of an implementation of experimental data showing the inhibitory effect of a *Plectranthus amboinicus* (PA) extract.

In the following detailed description of embodiments of the present disclosure, reference is made to the accompanying drawings in which like references indicate similar elements, and in which is shown by way of illustration specific embodiments in which the present disclosure may be practiced. These embodiments are described in sufficient detail to enable those skilled in the art to practice the present disclosure, and it is to be understood that other embodiments may be utilized and that logical, mechanical, biological, electrical, functional, and other changes may be made without departing from the scope of the present disclosure. The following detailed description is, therefore, not to be taken in a limiting sense, and the scope of the present disclosure is defined only by the appended claims. As used in the present disclosure, the term "or" shall be understood to be defined as a logical disjunction and shall not indicate an exclusive disjunction unless expressly indicated as such or notated as "xor."

The present disclosure relates to anti-inflammatory compositions. The methods and compositions address treatment of inflammation as well as treatment and prevention of inflammation-related diseases, disorders, and symptoms.

Inflammation-related disorders include, but are not limited to, autoimmune diseases, arthritis, allergies, cancers, heart diseases, stroke, arthrosclerosis, and Alzheimer's disease. Auto-immune diseases include acute disseminated encephalomyelitis (ADEM), ankylosing spondylitis (AS), coeliac diseases, Crohn's disease, Guillain-Barre syndrome (GBS), Hashimoto's disease, optic neuritis, Ord's thyroiditis, rheumatoid arthritis, and temporal arthritis.

According to the present disclosure, a method is provided for treating inflammation and inflammation-related disorders. The method comprises the steps of providing a composition containing at least *Plectranthus amboinicus* extract and administering a therapeutically effective amount of the composition to a patient in need thereof. According to implementations, a specific variety of *Plectranthus amboinicus* according to the present disclosure is unique to the island of Taiwan.

In another aspect of the present disclosure, a composition is provided for treating inflammation and inflammation-related disorders. The composition comprises a *Plectranthus amboinicus* extract.

The phrase "*Plectranthus amboinicus*" or "PA" refers to the *Plectranthus amboinicus* plant, which also includes any tissue, part or fraction therefrom or any preparation thereof including homogenates, suspension, filtrates, filtration residues and solution. Other names for *Plectranthus amboinicus* include Cuban oregano, Spanish thyme, Indian Borage, Mexican thyme, and Mexican mint.

The term "extract" refers to any solid, viscid, and liquid substance obtained through extraction from a given substance. In the present disclosure, a *Plectranthus amboinicus* extract includes any solid, viscid, and liquid substance extracted from *Plectranthus amboinicus* plant tissue.

Various methods and procedures for extraction are known and used by those skilled in the art. Such methods and procedures include both physical and chemical processes, including solvent utilization, distillation, percolation, and supercritical fluid extraction. The extract may be further filtered or concentrated as desired. In one example, a *Plectranthus amboinicus* extract is obtained by grinding homogenized *Plectranthus amboinicus* plant tissue and clarifying the crude extract with centrifugation.

In exemplary implementations, the *Plectranthus amboinicus* extract inhibits at least one of an IL-6, IL-12, MCP-1, and RANTES expression. The inhibition of IL-6, IL-12, MCP-1, and RANTES plays at least an anti-inflammatory role.

In some exemplary implementations, the *Plectranthus amboinicus* extract inhibits AP-1 binding activity. The inhibition of AP-1 binding activity plays a role in the prevention and therapy of diseases associated with excessive expression or activity of AP-1, for example, inflammatory diseases and immunological diseases.

In an aspect of the present disclosure, a method is provided for treating inflammation and inflammation-related disorders. The method comprises the steps of filtering *Plectranthus amboinicus* extract into at least one fraction, providing a composition having at least one of the *Plectranthus amboinicus* extract fractions, and administering a therapeutically effective amount of the composition to a patient in need thereof.

In another aspect of the present disclosure, a composition is provided for treating inflammation and inflammation-related disorders. The composition comprises at least one fraction of a *Plectranthus amboinicus* extract.

In exemplary implementations, the *Plectranthus amboinicus* extract fraction inhibits at least one of an IL-6, IL-12, MCP-1, and RANTES expression. In some exemplary implementations, the *Plectranthus amboinicus* extract fraction inhibits AP-1 binding activity.

The term "fraction" refers to one of the separable constituents of a substance. The fractions are collected based on differences in a specific property of the individual constituents. In exemplary implementations, the fractions are identified by their optical absorbance at a specific wavelength.

The term "filtering" refers to any procedure used to separate a constituent of a substance from other constituents of the substance. Various methods and procedures for filtration are known and used by those skilled in the art. Such methods and procedures include dialysis, gel filtration chromatography, and high-performance liquid chromatography (HPLC). In one example, *Plectranthus amboinicus* extract is filtered using a C-18 column.

The process of filtering may be repeated multiple times, where one or more of the fractions collected may be further filtered to generate additional fractions. In exemplary implementations, a filtered fraction of a *Plectranthus amboinicus* extract is filtered again into more fractions to further separate the constituents of the *Plectranthus amboinicus* extract. In one example, a filtered fraction is filtered with a C-18 column using a solvent gradient from 2% acetonitrile to 90% acetonitrile with 0.1% trifluoroacetic acid.

In exemplary implementations of the present disclosure, a *Plectranthus amboinicus* extract fraction, herein referred to as "F10" or "Fraction 10," contains a $C_{18}H_{17}NO_8$ compound, herein also referred to as "CHM9102," of the general structure:

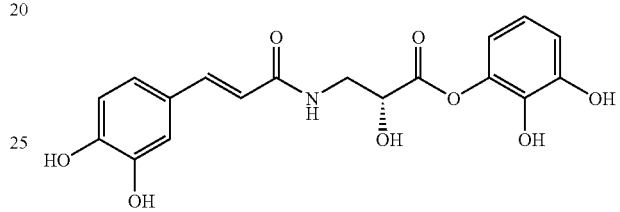

According to implementations, a method is provided for treating inflammation and inflammation-related disorders. The method comprises the steps of providing a composition comprising a compound of the general structure:

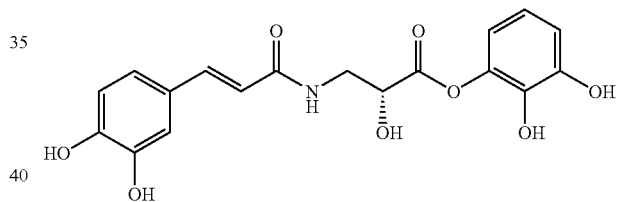

and administering a therapeutically effective amount of the composition to a patient in need thereof.

According to implementations, a composition is provided for treating inflammation and inflammation-related disorders. The composition comprises a compound of the general structure:

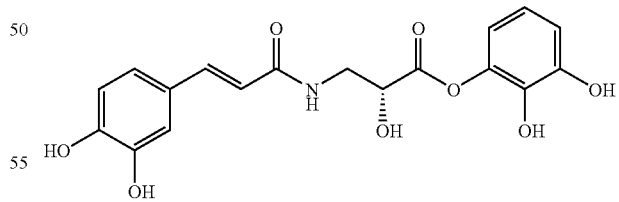

In exemplary implementations, the CHM9102 compound inhibits at least one of an IL-6, IL-12, MCP-1, and RANTES expression. In some exemplary implementations, CHM9102 inhibits AP-1 binding activity.

According to exemplary implementations, a composition may be in various forms including powders, creams, gels, salves, ointments, solutions, tablets, capsules, sprays, and patches. Vehicles and carriers may be used for delivery of the composition to the patient. Such carriers include solubilizing agents, diluents, and dispersion media. These carriers are biocompatible, pharmaceutically acceptable, and do not alter the treatment characteristics of the *Plectranthus amboinicus* extract or the CHM9102 compound. Excipients, adjuvants and other ingredients may also be included in the composition.

The composition should be stable during manufacture and storage. The *Plectranthus amboinicus* extract or the CHM9102 compound may be encapsulated, with agents such as aluminum monostearate, gelatin, and biodegradable and biocompatible polymers, to prevent undesired degradation in the body or by other ingredients in the composition. Anti-bacteria and anti-fungal agents such as benzyl alcohols, parabens, chlorobutanol, phenol, ascorbic acid, and thimerosal may also be included in the composition.

Administration of the composition may be achieved through various methods to different parts of the body, including intravenous, intradermal, subcutaneous, oral (e.g., inhalation), transdermal (i.e., topical), transmucosal, and rectal administration.

In exemplary implementations, the composition is a solution or suspension injected parenterally, intradermally, or subcutaneously. Carriers include water, saline solutions, and other synthetic solvents. Buffers such as acetates, citrates, and phosphates may be used, as well agents for adjusting tonicity, such as sodium chloride and dextrose, and agents for adjusting pH, such as hydrochloric acid and sodium hydroxide.

In other exemplary implementations, the composition is a dietary supplement. Dietary supplements may be prepared in various forms, including solid, liquid, and powder forms. The composition may be taken independently as a pill, tablet, or encapsulated gel, or as a food additive, beverage, or mixable powder.

The phrase "therapeutically effective amount" refers to an amount that produces some desired effect at a reasonable benefit/risk ratio applicable to any medical treatment. The effective amount may vary depending on such factors as the disease or condition being treated, the particular targeted constructs being administered, the size of the subject, or the severity of the disease or condition. One of ordinary skill in the art may empirically determine the effective amount of a particular compound without necessitating undue experimentation.

According to another aspect of the present disclosure, a CHM9102 analog may be used instead of CHM9102 for treating inflammation and inflammation-related disorders. In exemplary implementations, a CHM9102 analog, herein referred to as "rosmarinic acid," may be used instead of CHM9102. The rosmarinic acid has the general structure:

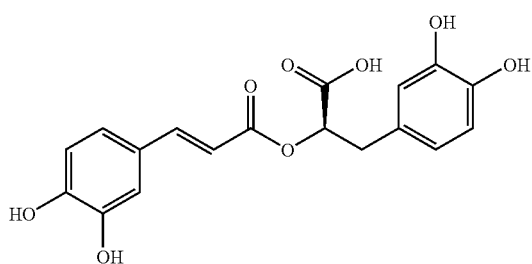

According to implementations, a method is provided for treating inflammation and inflammation-related disorders. The method comprises the steps of providing a composition comprising a compound of the general structure:

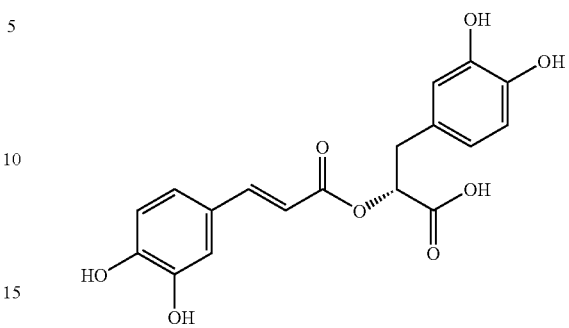

and administering a therapeutically effective amount of the composition to a patient in need thereof.

According to implementations, a composition is provided for treating inflammation and inflammation-related disorders. The composition comprises a compound of the general structure:

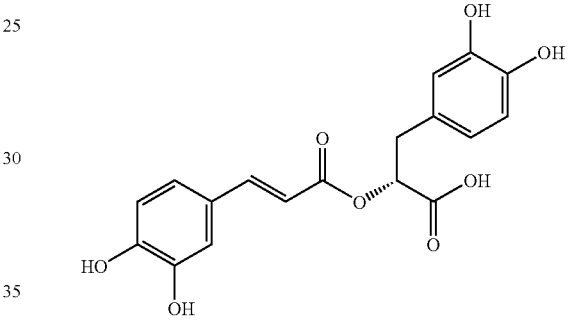

In exemplary implementations, the rosmarinic acid compound inhibits at least one of an IL-6, IL-12, MCP-1, and RANTES expression. In some exemplary implementations, rosmarinic acid inhibits AP-1 binding activity.

Figure 5:
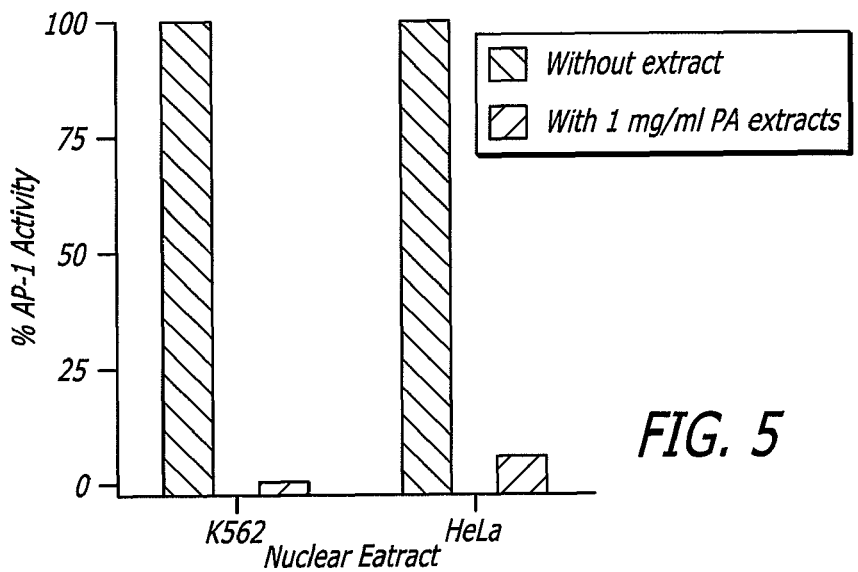
FIG. 5 is a graph of an implementation of experimental data showing the AP-1 inhibition activities of *Plectranthus amboinicus* extracts.

As discussed, *Plectranthus Amboinicus* has AP-1 inhibition activity, as shown in FIG. 5. Therefore, the *Plectranthus Amboinicus* extract and its active ingredients (alone or in combination) are useful for treating inflammation-related diseases, such as rheumatoid arthritis and others.

According to implementations of experimental data shown in FIG. 5, oligonucleotide containing AP-1 binding sites were incubated nuclear extracts from TPA-stimulated K562 (K562) or HeLa (HeLa) cells. The antibodies to AP-1 complexes were added followed with horseradish peroxidase-labeled secondary antibody for ELISA-based analysis. AP-1 binding activity in the nuclear extract from TPA-stimulated cells was defined as 100% and the AP-1 binding activity of buffer only was defined as 0%. Data showed PA extract can inhibit AP-1 binding activities.

Figure 6:
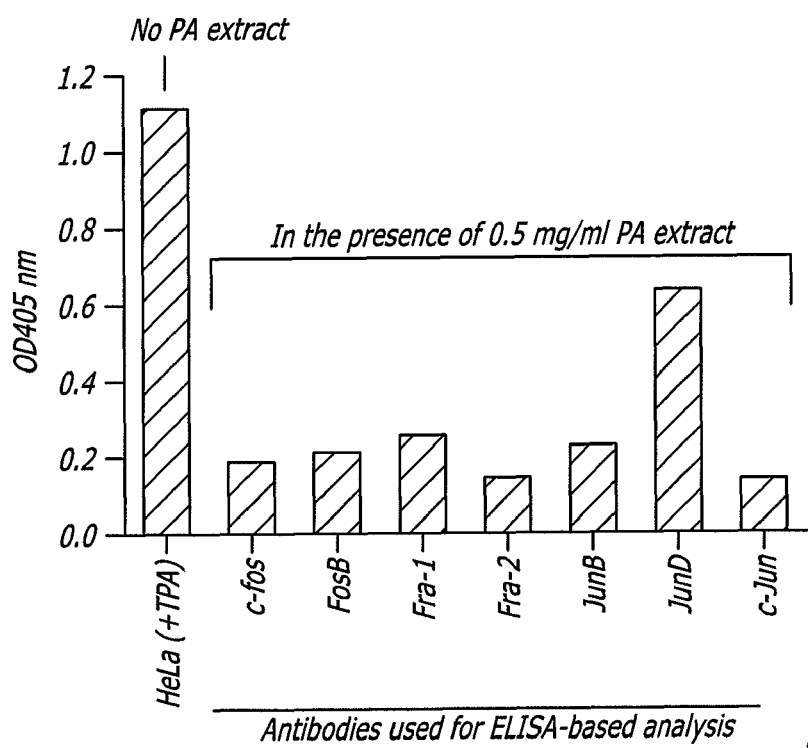
FIG. 6 is a graph of an implementation of experimental data showing PA extract can inhibit AP-1 complexes formed by different component proteins.

According to an implementation, AP-1 complexes can be formed, but not limited, by C-Jun, JunB, JunD, c-Fos, Fos-B, Fra-1 or Fra-2. As shown in FIG. 6, the binding activities of AP-1 complexes formed by the indicated proteins were decreased in the presence of *Plectranthus amboinicus* extracts.

According to implementations of experimental data shown in FIG. 6, AP-1 complexes can be formed by different proteins such as C-Jun, JunB, JunD, c-Fos, Fos-B, Fra-1 or Fra-2. Various antibodies were used in ELISA-based analysis to demonstrate the target protein for PA extract. Results showed that PA extract can inhibit DNA-binding activities of the complexes formed by C-Jun, JunB, JunD, c-Fos, Fos-B, Fra-1 or Fra-2.

Thus, rosmarinic acid, Mena 987, Mena 998, Mena 9102 are present in a *Plectranthus amboinicus* extract which has AP-1 inhibition activity. According to implementations, the *Plectranthus amboinicus* extract are useful for treating rheumatoid arthritis or other inflammation-related diseases when used in pharmaceutical or nutraceutical compositions.

According to implementations, *Plectranthus amboinicus* extracts contain 0.5-1.2% (e.g., 0.89%) by weight rosmarinic acid, 0.05-0.1% (e.g., 0.06%) by weight Mena 987, 0.05-0.1% (e.g., 0.09%) by weight Mena 998, and 0.05-0.1% (e.g., 0.08%) by weight Mena 9102. The percentage of polyphenols in the extract may be at least 30% (i.e., any integer percentage between 30% and 100%, inclusive) by weight, as determined using the hide powder method, which has been the official method for polyphenol analysis (American Leather Chemist Association). The amount of polyphenols is determined by preparation of polyphenols solutions, absorption of the polyphenols on chromated fide powder, and subsequent determination of residual materials by gravimetric analysis.

According to implementations, the extract is prepared according to the methods described in Examples below or by equivalent methods. For example, the crude leaf juice is centrifuged at 10000×g for 30 min, and the supernatant is filtered. The filtrate is lyophilized to yield a dry powder. Then power is purified by RPC18-HPLC. According to the elution profile and implementations, four fractions were collected by a model CHF122SB Advantec fraction collector. Frac #8 (contained Mena 987) was collected from 19.5 to 21.5 min, Frac #9 (contained Mena 998) was collected from 21.5 to 23.5 min, Frac #10 (contained rosmarinic acid and Mena 9102) was collected from 23.5 to 25.5 min According to implementations, 1 g *Plectranthus amboinicus* dry powder can yields 4.8 mg Frac#8, 14 mg Frac#9 and 12.7 mg Frac#10.

According to implementations, a pharmaceutical composition Mena 987 is disclosed comprising a therapeutically effective amount of:

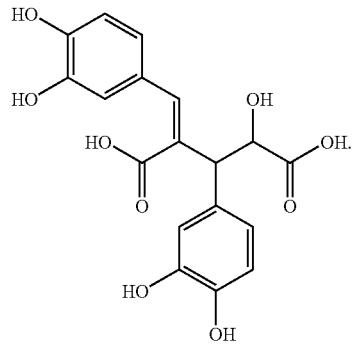

According to implementations, a composition Mena 998 is disclosed comprising a therapeutically effective amount of at least one of:

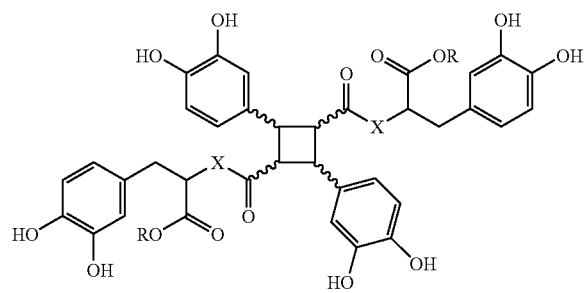

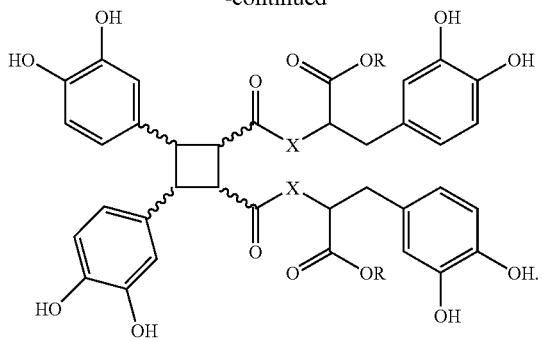

According to implementations, a composition Mena 9102 is disclosed comprising a therapeutically effective amount of:

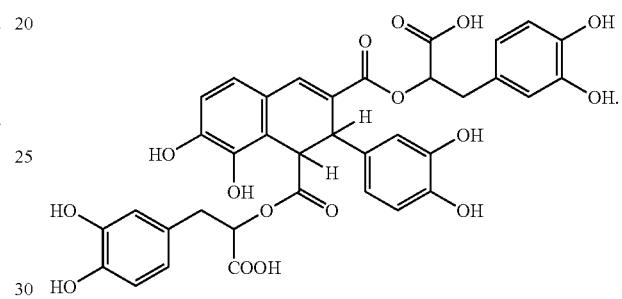

According to implementations, a composition rosmarinic acid is disclosed comprising a therapeutically effective amount of:

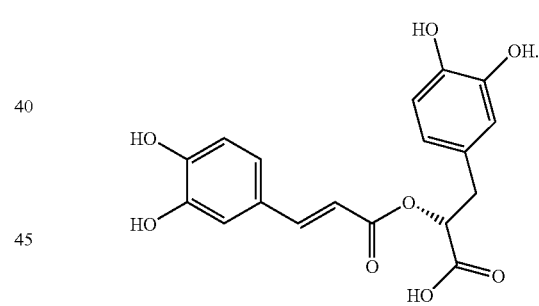

As the biological functions of rosmarinic acid, Mena 987, Mena 998, and Mena 9102 differ, the proportion of each ingredient in the PA extract may be adjusted as needed. For improved bioactivity, some analogues may be synthesized artificially.

According to implementations, a composition is disclosed comprising an inhibition of AP-1 with an effective amount of formula I.

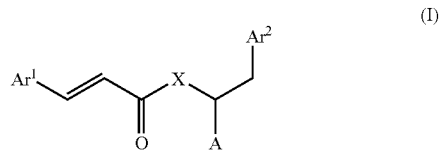

Where $Ar^1$ and $Ar^2$ are independently selected from phenyl, mono-, di- and multi-substituents phenyl, for example, $(HO)_n$, $(H_3CO)_n$ where n=1-3, methylenedioxy ($OCH_2O$), $CH_3$, F, Cl, Br, I, NHR (R=H, $OCOCH_3$), $NO_2$, and COOR; where R is H or alkyl, and RCO, where R is H or alkyl; A is independently selected from H, COOR, CONRR', $SO_3H$, $SO_2NRR'$, or PO(OR)(OR'), where R and R' are independently selected from H, C1-C6 alkyl, or aryl; and where X is $CH_2$, O, or NH.

According to implementations, a composition is disclosed comprising a therapeutically effective amount of one of the compounds of Table 1:

$CH_3$, F, Cl, Br, I, NHR (R=H, $OCOCH_3$), $NO_2$, COOR where R is H or alkyl, and RCO where R is H or alkyl, X is $CH_2$, O, NH. $R^1$ are independently selected from H, C1-C6 alkyl, aryl, $R^2$ are independently selected from COOH, COOEt, aryl, hydroxyl-aryl.

According to implementations, a composition is disclosed comprising a therapeutically effective amount of one of the compounds of Table 2:

TABLE 2

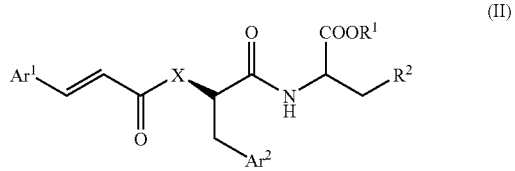

| Ar¹ | X | Ar² | R¹ | R² |
|---|---|---|---|---|
| 3,4-dihrdroxy phenyl | O | 3,4-dihrdroxy phenyl | Me | 3,4-dihrdroxy phenyl (13) |
| 3,4-dihrdroxy phenyl | O | 3,4-dihrdroxy phenyl | Et | 3,4-dihrdroxy phenyl (14) |
| 3,4-dihrdroxy phenyl | O | 3,4-dihrdroxy phenyl | H | COOH (15) |
| 3,4-dihrdroxy phenyl | O | 3,4-dihrdroxy-6-nitro-phenyl | Me | 3,4-dihrdroxy phenyl (16) |
| 3,4-dihrdroxy phenyl | O | 3,4-dihrdroxy phenyl | Me | 3-1H-indole (17) |
| 3,4-dihrdroxy phenyl | O | 3,4-dihrdroxy phenyl | H | 3-1H-indole (18) |
| 3,4-dihrdroxy phenyl | NH | 3,4-dihrdroxy phenyl | Me | 3,4-dihrdroxy phenyl (19) |
| 3,4-dihrdroxy phenyl | NH | 3,4-dihrdroxy phenyl | H | 3,4-dihrdroxy phenyl (20) |
| 3,4-dihrdroxy phenyl | NH | 3,4-dihrdroxy-6-nitro-phenyl | H | 3,4-dihrdroxy phenyl (21) |

TABLE 1

| Ar¹ | X | A | Ar² |
|---|---|---|---|
| 3,4-dihrdroxy phenyl | NH | COOMe | 3,4-dihrdroxy phenyl (5) |
| 3,4-dihrdroxy phenyl | NH | COOEt | 3,4-dihrdroxy phenyl (6) |
| 3,4-dihrdroxy phenyl | NH | COOH | 3,4-dihrdroxy phenyl (7) |
| 3,4-dihrdroxy phenyl | NH | H | 3,4-dihrdroxy phenyl (8) |
| 3,4-dihrdroxy phenyl | NH | $PO(OEt)_2$ | 3,4-dihrdroxy phenyl (9) |
| 3,4-dihrdroxy phenyl | O | COOEt | 3,4-dihrdroxy phenyl (10) |
| 3,4-dihrdroxy-6-nitro-phenyl | O | COOH | 3,4-dihrdroxy-6-nitro-phenyl (11) |
| 3,4-dihrdroxy-6-nitro-phenyl | O | COOH | 3,4-dihrdroxy-6-nitro-phenyl (12) |

According to implementations, a composition is disclosed comprising a therapeutically effective amount of formula II.

(II)

Where $Ar^1$ and $Ar^2$ are independently selected from phenyl, mono-, di- and multi-substituents phenyl, for example, $(HO)_n$, $(H_3CO)_n$ where n=1-3, methylenedioxy ($OCH_2O$), To test the effect of the compounds of the present disclosure on AP-1 binding activity to AP-1 recognition sequence, ELISA experiments were performed. The results of the AP-1 inhibition assay results are shown in Table 3.

TABLE 3

| Example no. | IC$_{50}$ (µM) |
|---|---|
| Mena 987 (1) | 4.3 ± 2.6 |
| Mena 998 (2) | 0.9 ± 0.5 |
| Mena 9102 (3) | 1.4 ± 0.9 |
| rosmarinic acid (4) | 10.0 ± 4.1 |
| 5 | 39.0 ± 31.0 |
| 6 | 32.5 ± 24.0 |
| 7 | 9.2 ± 3.2 |
| 8 | 12.9 ± 5.9 |
| 9 | 26.2 ± 18.9 |
| 10 | 5.6 ± 4.2 |
| 11 | 21.3 ± 24.0 |
| 12 | 35.5 ± 20.1 |
| 13 | 0.8 ± 0.8 |
| 14 | 1.2 ± 0.8 |
| 15 | 34.7 ± 21.3 |
| 16 | 21.3 ± 24.0 |
| 17 | 43.4 ± 28.2 |
| 18 | 31.9 ± 20.0 |
| 19 | 8.0 ± 4.7 |
| 20 | 3.5 ± 2.0 |
| 21 | 30.7 ± 18.1 |

Figure 7:
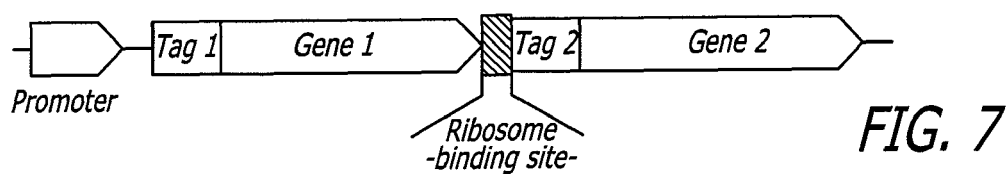
FIG. 7 is a schematic of an implementation of experimental data showing co-expression of Gene X and Y in a bicistronic expression system.
Figure 9A:
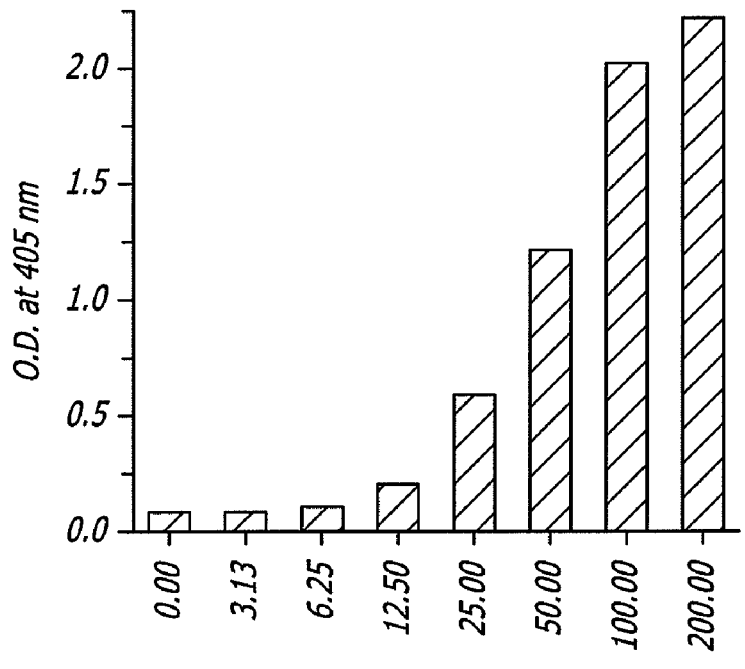
FIG. 9 is a graph of an implementation of experimental data showing development of assays for AP-1 DNA binding activities.
Figure 9B:
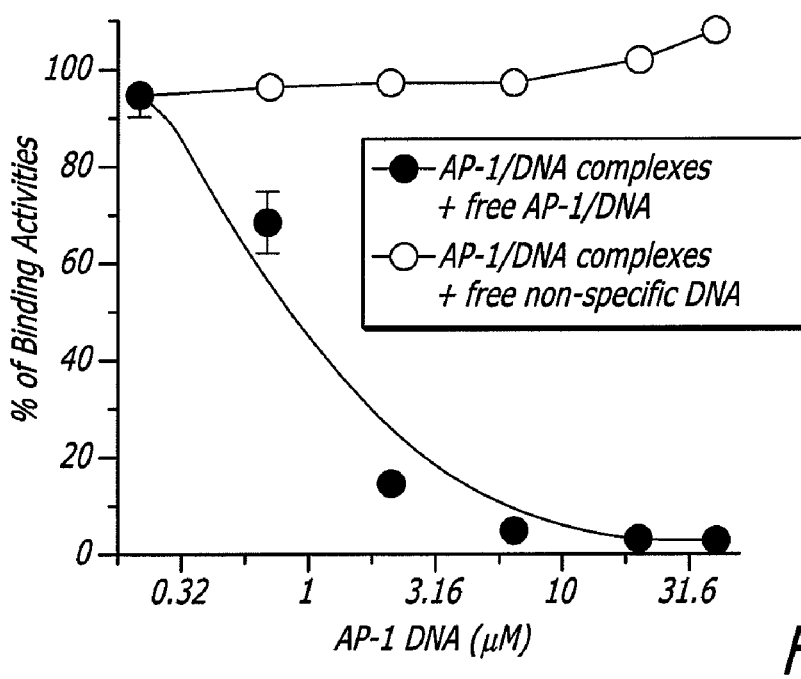
Figure 9C:
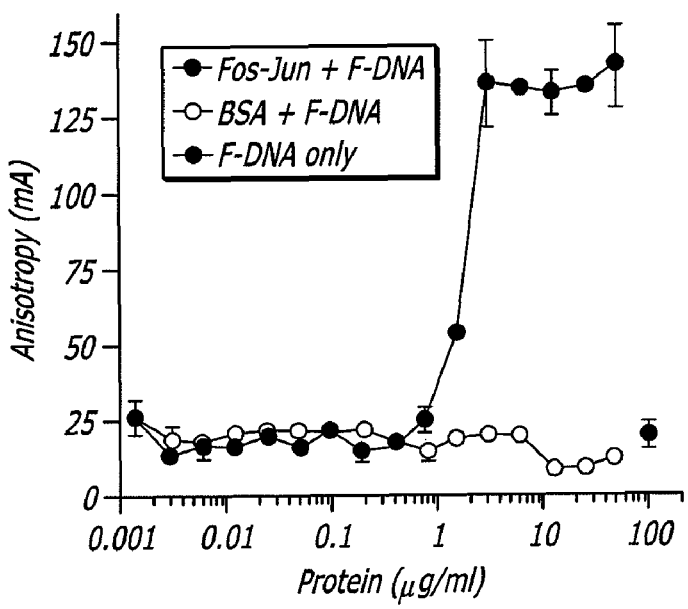
Figure 9D:
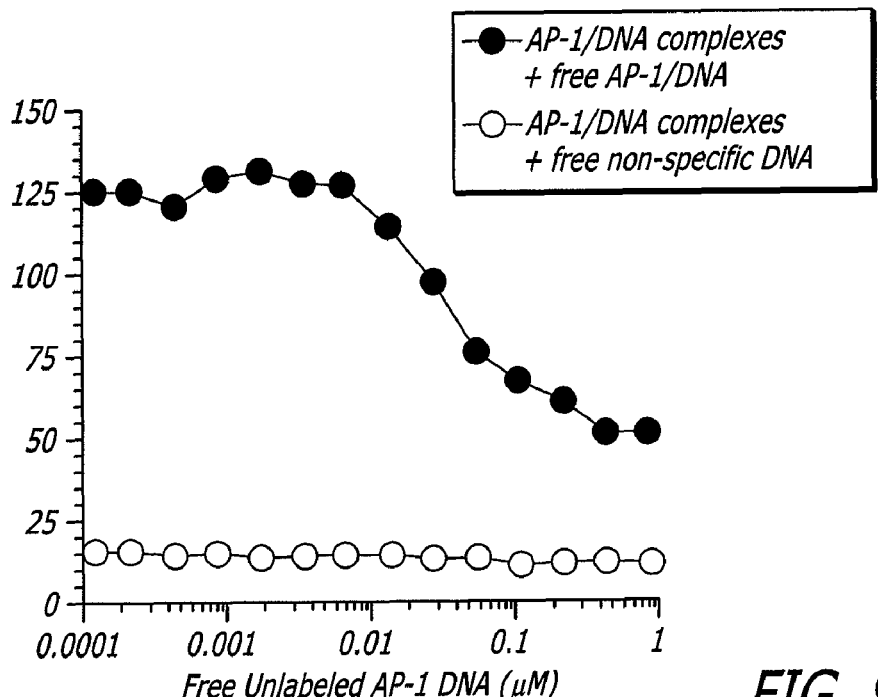

According to implementations, binding assays were developed to identify inhibitors that block the AP-1 DNA binding activities. Traditional methods call for the preparation of nuclear extracts from TPA-stimulated cells, or require separate purification of Fos and Jun followed with in vitro dimerization to form a functional AP-1 complexes. A bicistronic expression vector that can drive the expression of two genes in one plasmid was thus designed as shown in FIG. 7. In this system, a promoter would directly drive the expression of the first gene, which is connected to the second gene via a ribosome-binding site in order to confer the expression of the second genes. Any pair of genes that form heterodimer in the cells for their physiological functions can be potentially expressed as complexes in the cells using this system.

According to implementations, the expression system of FIG. 7 was used to co-express AP-1 complexes. Accordingly, Fos (as gene 1) was tagged with a (Histidine)$_6$ tag and Jun (as Gene 2) was tagged with Strep-tag as illustrated in FIG. 8A. The results demonstrated that complexes containing both his-tagged and strep-tagged protein are purified with $Ni^{2+}$ chromatography using a single step (FIG. 8B). Cross-linking experiments further confirmed the Fos-Jun complexes are dimers (FIG. 8C).

According to implementations of experimental data shown in FIG. 8, a construct for bicistronic expression of Fos and Jun in a single vector, such as a plasmid, was created as shown in FIG. 8A. In FIG. 8B, purification of recombinant Fos-Jun complexes was accomplished. Bacterial cells harboring pFos-Jun were induced for recombinant protein expression. After cell lysis, the cell crude extracts were passed through $Ni^{2+}$ column followed with imidazole elution to release (Histidine)$_6$-containing complexes. As shown in FIG. 8B, lane M is a protein marker; lane 1 is a cell crude extract; lane 2 is flow-through from $Ni^{2+}$ column; lane 3 is a wash with 10 mM imidazole; and lane 4 is elution with 500 mM imidazole.

The crude extracts containing or the purified proteins were used for ELISA-based and fluorescence anisotropy-based binding analysis. Labeled oligonucleotides containing one or more copies of AP-1 consensus binding sites were used in the binding assays. Biotin-labeled oligonucleotides were used to coat streptavidin-plates in ELISA-binding assays. Rhodamine or fluorescein or other fluorophores-labeled oligonucleotides were used for fluorescence anisotropy analysis.

As shown in FIG. 9, the results confirmed that the DNA binding activities of recombinant AP-1 complexes were specific as potent competitors, as free unlabeled oligonucleotides containing AP-1 consensus binding sites block the binding between labeled DNA and the AP-1 complexes using both ELISA- and fluorescence anisotropy-based binding assays. According to implementations shown in FIG. 9, development of ELISA-based (FIGS. 9A and 9B) and fluorescence anisotropy-based (FIGS. 9C and 9D) assays for AP-1 DNA binding activities. FIGS. 9A and 9C show concentration-dependent increase in AP-1 binding activities. FIGS. 9B and 9D show dose-dependent inhibition by free AP-1-binding site-containing oligonucleotides.

According to implementations, the compounds of the present disclosure can be included in a pharmaceutical or nutraceutical composition together with additional active agents, carriers, vehicles, excipients, or auxiliary agents identifiable by a person skilled in the art upon reading of the present disclosure and administered to at least the eye of an animal, such as human.

The pharmaceutical or nutraceutical compositions preferably comprise at least one pharmaceutically acceptable carrier. In such pharmaceutical compositions, the agents of the present disclosure are the "active compound," also referred to as the "active agent." As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions. A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol, or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates, or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Subject as used herein refers to humans and non-human primates (e.g., guerilla, macaque, marmoset), livestock animals (e.g., sheep, cow, horse, donkey, and pig), companion animals (e.g., dog, cat), laboratory test animals (e.g., mouse, rabbit, rat, guinea pig, hamster), captive wild animals (e.g., fox, deer), and any other organisms who can benefit from the agents of the present disclosure. There is no limitation on the type of animal that could benefit from the presently described agents. A subject regardless of whether it is a human or non-human organism may be referred to as a patient, individual, animal, host, or recipient.

Pharmaceutical compositions suitable for an injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition should be sterile and should be fluid to the extent that easy syringability exists. It should be stable under the conditions of manufacture and storage and be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, methods of preparation include vacuum drying and freeze-drying, which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be transmucosal or transdermal. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration may be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

According to implementations, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to cell-specific antigens) can also be used as pharmaceutically acceptable carriers. These can be prepared according to methods known to those skilled in the art, for example, as described in U.S. Pat. No. 4,522,811, which is incorporated by reference herein.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds may be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects can be used, care should be taken to design a delivery system that targets such compounds to the site of affected location to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the disclosure, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of the active compound (i.e., an effective dosage) may range from about 0.001 to 100 g/kg body weight, or other ranges that would be apparent and understood by artisans without undue experimentation. The skilled artisan will appreciate that certain factors can influence the dosage and timing required to effectively treat a subject, including but not limited to the severity of the disease or disorder, previous treatments, the general health or age of the subject, and other diseases present.

According to another aspect, one or more kits of parts can be envisioned by the person skilled in the art, the kits of parts to perform at least one of the methods herein disclosed, the kit of parts comprising two or more compositions, the compositions comprising alone or in combination an effective amount of the agents of the present disclosure according to the at least one of the above mentioned methods.

The kits possibly include also compositions comprising active agents other than the compounds of the present disclosure, identifiers of a biological event, or other compounds identifiable by a person skilled upon reading of the present disclosure. The term "identifier" refers to a molecule, metabolite or other compound, such as antibodies, DNA or RNA oligonucleotides, able to discover or determine the existence, presence, or fact of or otherwise detect a biological event under procedures identifiable by a person skilled in the art; exemplary identifiers are antibodies, exemplary procedures are western blot, nitrite assay and RT-PCR, or other procedures as described in the Examples. Exemplary biological events are cytokine expression or other immunomodulating events.

The kit can also comprise at least one composition comprising an effective amount the compounds of the present disclosure or a cell line. The compositions and the cell line of the kits of parts to be used to perform the at least one method herein disclosed according to procedure identifiable by a person skilled in the art.

EXAMPLES

A more complete understanding of the present disclosure can be obtained by reference to the following specific examples and figures. The examples and figures are described solely for purposes of illustration and are not intended to limit the scope of the disclosure. Changes in form and substitution of equivalents are contemplated as circumstances may suggest or render expedient. Although specific terms have been employed herein, such terms are intended in a descriptive sense and not for purposes of limitations. Modifications and variations of the disclosure as hereinbefore set forth can be made without departing from the spirit and scope thereof, and, therefore, only such limitations should be imposed as are indicated by the appended claims.

Example 1

Anti-Inflammatory Activity of PA Extract

The effects of PA on the LPS (lipopolysaccharide)-induced expression of 17 cytokines and five chemokines are shown in Table 1. Human umbilical vein endothelial (HUVEC) cells were incubated with LPS in the absence or presence of 1 mg/ml crude extract of PA. The cytokine expression profile was determined using Luminex. Results showed that the crude extract of PA can significantly reduce the expression of the cytokines IL-6, IL-8, IL-12, MCP-1, and RANTES.

TABLE 1

Effects of PA extract on the LPS-induced expression.

|  | Control | LPS | Indomethacin LPS | PA LPS |
|---|---|---|---|---|
| IL-1a | 13.2 | 13.8 | 13.8 | 13.6 |
| IL-1b | 11.6 | 11.7 | 11.7 | 11.7 |
| IL-2 | 10 | 10.1 | 10.1 | 10.1 |
| IL-3 | 8.85 | 8.86 | 8.82 | 8.8 |
| IL-4 | 11.7 | 11.9 | 11.8 | 11.6 |
| IL-5 | 1.19 | 1.23 | 1.24 | 1.19 |
| IL-6 | 280 | 69800 | 62300 | 36600 |
| IL-7 | 32 | 56.7 | 51.5 | 51.5 |
| IL-8 | 1970 | 10100 | 8030 | 7480 |
| IL-10 | 1.07 | 1.11 | 1.12 | 1.11 |
| IL-12 (p40) | <3 | 12.5 | 16.4 | 8.8 |
| IL-12 (p70) | 6.42 | 6.43 | 6.43 | 6.41 |
| IL-13 | 11.1 | 11.1 | 11.1 | 11.1 |
| IL-15 | 13.2 | 13.5 | 13.4 | 13.3 |
| IP-10 | 18.8 | 22.9 | 24.5 | 19.9 |
| Eotaxin | 55.3 | 35.9 | 29.1 | 28.8 |
| IFNg | 1.4 | 2.02 | 2.41 | 2.86 |
| GM-CSF | 10.2 | 169 | 220 | 130 |
| MCP-1 | 388 | 79300000 | 41800 | 154000 |
| MIP-la | 6.89 | 7.31 | 7.57 | 7.08 |
| RANTES | <1 | 4.68 | 5.48 | 2.22 |
| TNFa | 8.17 | 8.28 | 8.14 | 8.19 |

Example 2

Inhibition of AP-1 Binding Activities with PA Extract

Due to the involvement of AP-1 activity in inflammatory signaling, the effects of the PA crude extract on AP-1/DNA binding activity was examined. Shown in FIG. 1, an ELISA-based assay was used to determine the inhibitory effects of the PA crude extract on DNA binding activity of AP-1 transcription factors. The nuclear extract prepared from TPA-activated HeLa or K562 cells were used as AP-1 protein sources. After incubating with the oligonucleotides containing AP-1 binding sites, the AP-1/DNA complexes were detected with HRP-conjugated anti-c-Fos antibodies. It was found that the DNA binding activity of AP-1 in vitro was inhibited by the PA crude extract and the effects were dose-dependent.

Example 3

Figure 2:
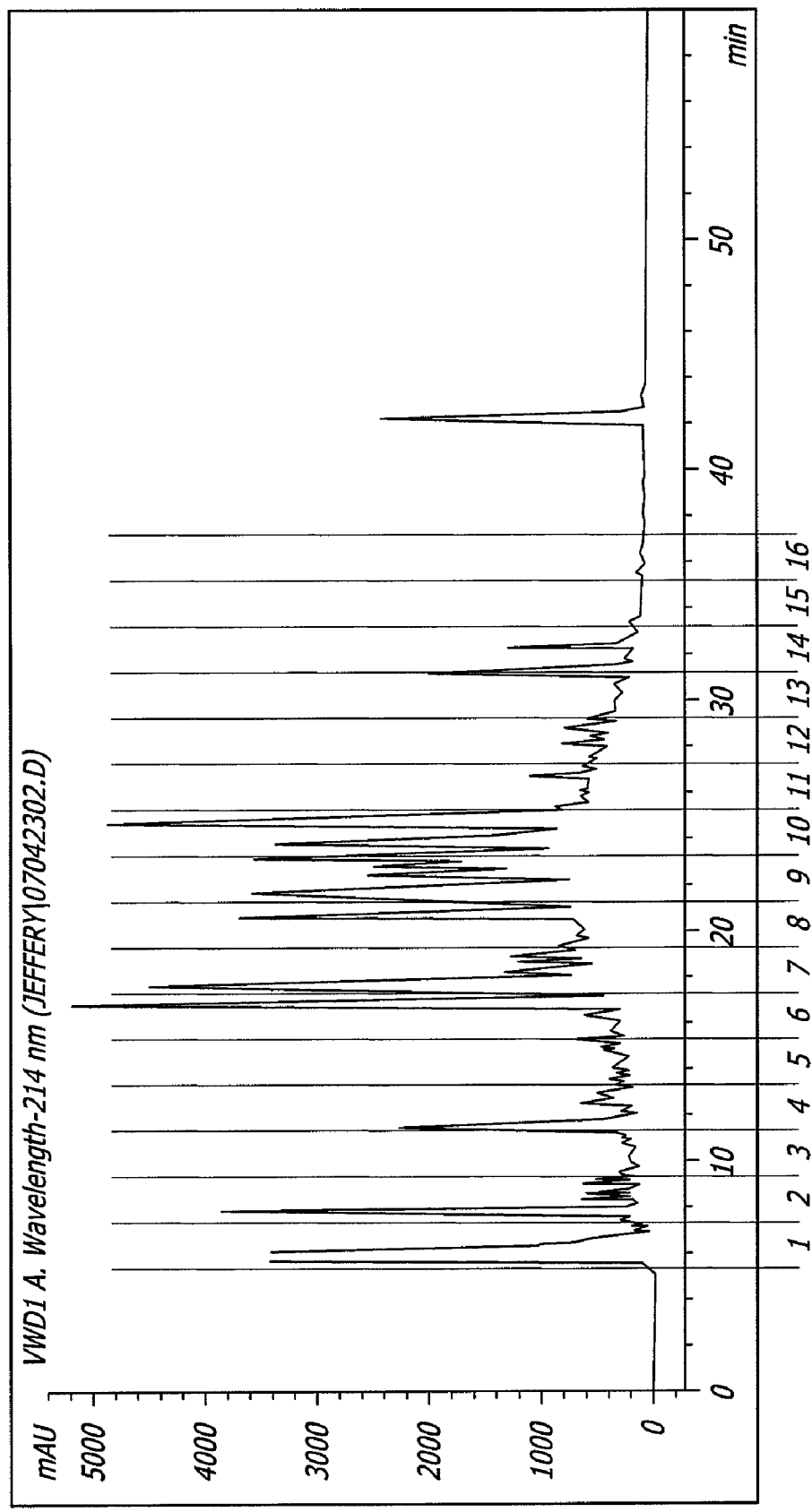
FIG. 2 is an HPLC graph of an implementation of the fractionation of the *Plectranthus amboinicus* extract.
Figure 3:
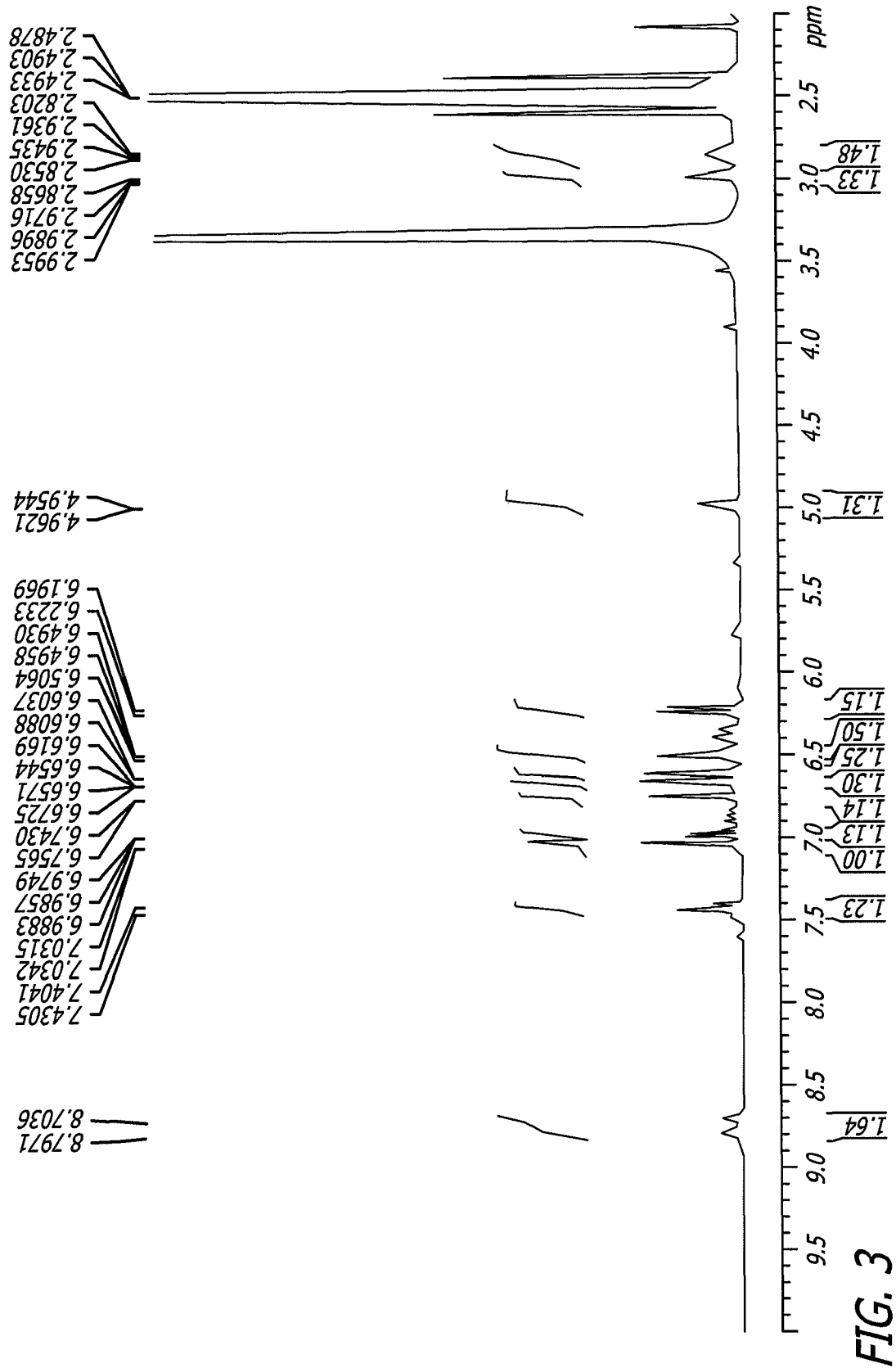
FIG. 3 is an NMR spectroscopy graph of CHM9102.
Figure 4A:
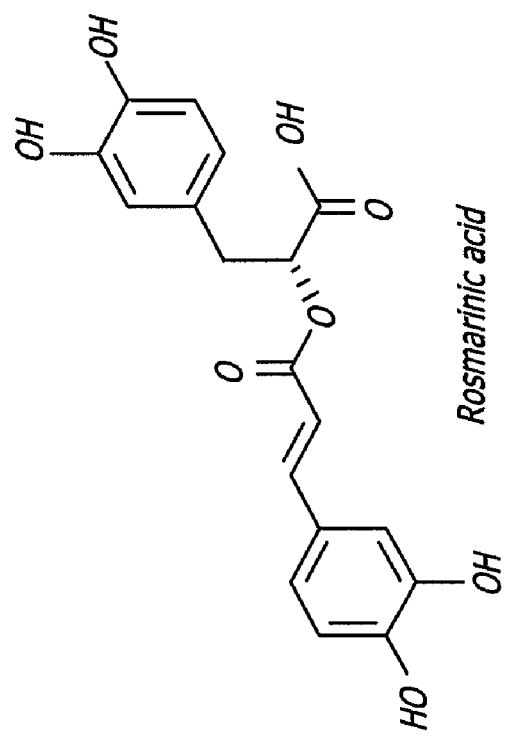
FIG. 4 shows the chemical structure and bar graphs showing the inhibitory effects of CHM9102 and rosmarinic acid.
Figure 4A:
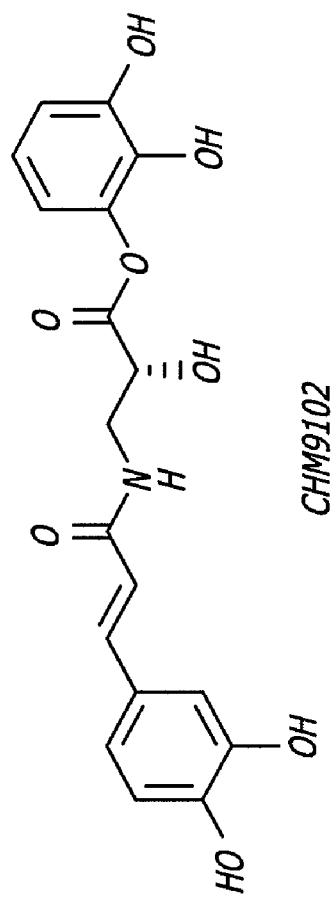
Figure 4B:
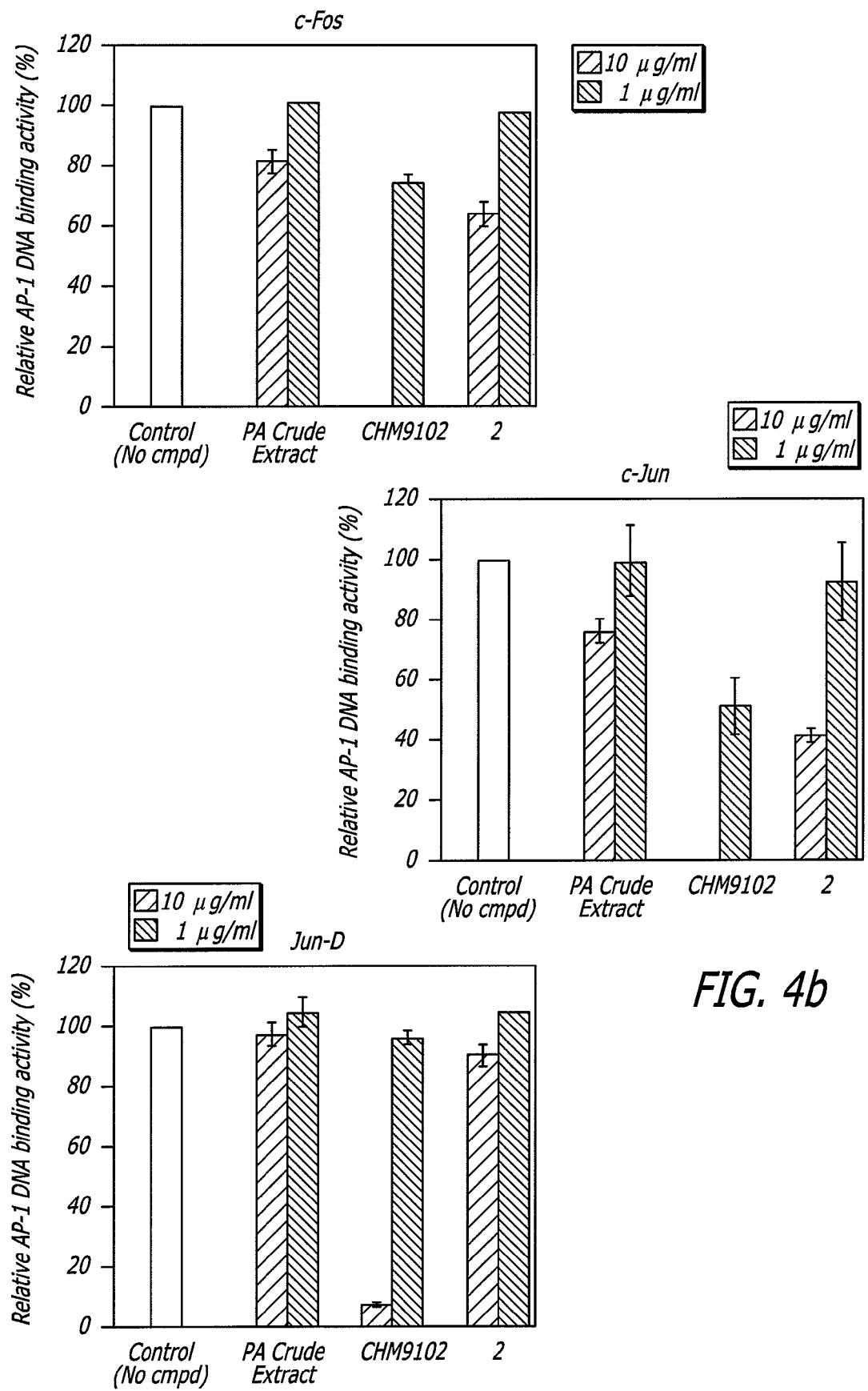

Inhibition of AP-1 Binding Activities with Fraction 10, CHM9102, and Rosmarinic Acid The PA crude extract was further fractionated with preparative HPLC using C18 column. As shown in FIG. 2, the crude extract of *Plectranthus amboinicus* was separated into 16 fractions. Fraction 10 showed inhibitory effects against AP-1 binding. This fraction was further purified by employing another C18 column using the solvent gradient from 2% acetonitrile to 90% acetonitrile containing 0.1% trifluoroacetic acid. The major peak was collected and then subjected for structural determination by MASS and NMR analysis, shown in FIG. 3. These studies resulted in the deduction of the structure of the active component, CHM9102. Rosmarinic acid, an analog of the CHM9102, was also tested for AP-1 inhibitory activities.

While the method and agent have been described in terms of what are presently considered to be the most practical and preferred implementations, it is to be understood that the disclosure need not be limited to the disclosed exemplary implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

Example 4

Mena 987 Purification

According to implementations, Frac#8 dry powder was reconstituted in 50% acetonitrile water mixture with 0.1% trifluoroacetic acid. The established HPLC system was described as above. In the $RPC_{18}$-HPLC experiments, Frac#8 was monitored at 214 nm. A linear gradient from 90% solvent A (98% water, 2% acetonitrile, and 0.1% trifluoroacetic acid) to 30% solvent B (90% acetonitrile, 10% water, and 0.1% trifluoroacetic acid) in 60 min was used to purify Mena 987. The column was re-equilibrated with 90% solvent A for 20 min prior to each injection. In our experiment, peaks were collected by a model CHF122SB Advantec fraction collector. Mena 987 was found in the peak with $T_R$=13 min as a single compound identified by mass spectrometry. The structure of Mena 987 was identified by MASS, NMR. 1 g *Plectranthus amboinicus* dry powder can yield 0.6 mg Mena 987.

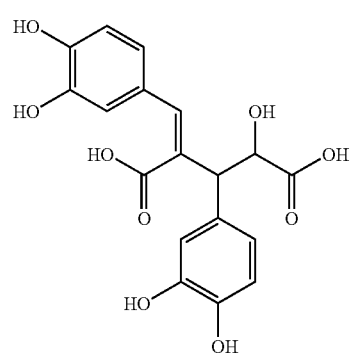

(1)

$^1$H NMR (600 MHz, $D_2O$) $\delta$7.69 (d, J=1.6 Hz, 1H), 6.95-6.97 (m, 2H), 6.89 (d, J=2.0 Hz, 1H), 6.82-6.86 (m, 2H), 6.77 (dd, J=8.2, 2.1 Hz, 1H), 4.91 (d, J=2.5 Hz, 1H); 4.66 (dd, J=2.5, 2.5 Hz, 1H); $^{13}$C NMR (150 MHz, $D_2O$): $\delta$175.1, 175.1, 147.0, 144.4, 143.8, 143.4, 140.1, 132.2, 125.8, 125.3, 122.3, 119.5, 118.2, 116.5, 115.9, 115.0, 83.7, 48.1.

Example 5

Mena 998 Purification

According to implementations, Frac#9 dry powder was reconstituted in 50% acetonitrile water mixture with 0.1% trifluoroacetic acid. The established HPLC system was described as above. In the $RPC_{18}$-HPLC experiments, Frac#9 was monitored at 214 nm. A linear gradient from 90% solvent A (98% water, 2% acetonitrile, and 0.1% trifluoroacetic acid) to 25% solvent B (90% acetonitrile, 10% water, and 0.1% trifluoroacetic acid) in 60 min was used to purify Mena 998. The column was re-equilibrated with 90% solvent A for 20 min prior to each injection. Peaks were further collected by a model CHF122SB Advantec fraction collector. Mena 998 was found in the peak with $T_R$=34.5 min as a single compound identified by mass spectrometry. The structure of Mena 987 was identified by NMR and high resolution mass (HRMS). 1 g *Plectranthus Amboinicus* dry powder can yields 0.9 mg Mena 998.

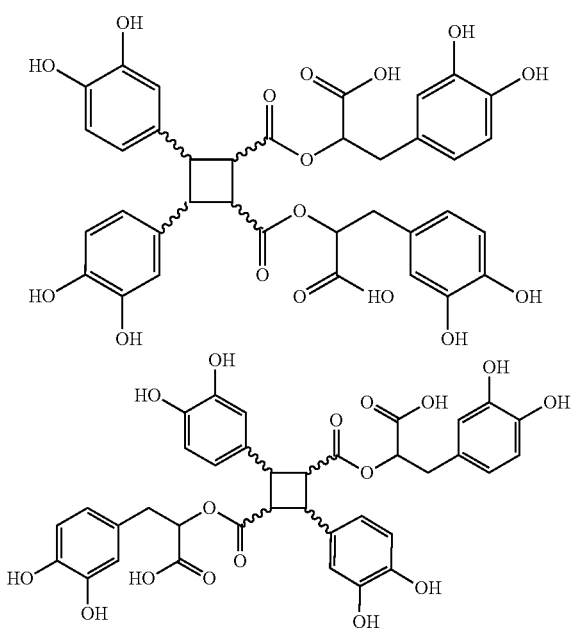

(2)

$^1$H NMR (600 MHz, D$_2$O) δ6.70-6.88 (m, 9H), 6.56 (m, 2H), 6.12 (d, J=8.2 Hz, 1H), 4.55 (m, 2H), 4.23 (m, 2H), 3.88 (dd, J=8.6, 8.6 Hz, 1H), 3.78 (dd, J=10.5, 6.4 Hz, 1H), 3.01 (dd, J=14.2, 3.5 Hz, 1H), 2.85 (dd, J=14.0, 9.8 Hz, 1H), 2.78 (dd, J=14.3, 7.5 Hz, 1H), 2.71 (dd, J=14.4, 4.6 Hz, 1H); $^{13}$C NMR (150 MHz, D$_2$O) δ175.3, 173.7, 173.1, 144.0, 143.8, 143.7, 143.6, 143.0, 142.8, 142.7, 131.1, 130.8, 129.6, 129.1, 122.0, 121.8, 120.1, 118.4, 117.1, 116.9, 116.2, 116.0, 115.7, 115.0, 76.2, 75.6, 47.5, 46.1, 41.0, 40.4, 36.5, 36.0. HRMS calculated for C$_{36}$H$_{32}$O$_{16}$ [M+H]$^+$: 721.1769, found: 721.1841.

Example 6

Mena 9102 Purification

According to implementations, Frac#10 dry powder was reconstituted in 50% acetonitrile water mixture with 0.1% trifluoroacetic acid. The established HPLC system was described as above. In the RPC$_{18}$-HPLC experiments, Frac#10 was monitored at 214 nm. A linear gradient from 80% solvent A (98% water, 2% acetonitrile, and 0.1% trifluoroacetic acid) to 25% solvent B (90% acetonitrile, 10% water, and 0.1% trifluoroacetic acid) in 60 min was used to purify Mena 9102. The column was re-equilibrated with 80% solvent A for 20 min prior to each injection. Peaks were further collected by a model CHF122SB Advantec fraction collector. Mena 9102 was found in the peak with $T_R$=24.5 min as a single compound identified by mass spectrometry. The structure of Mena 987 was identified by NMR and high resolution mass (HRMS). 1 g *Plectranthus Amboinicus* dry powder can yields 0.8 mg Mena 9102.

(3)

$^1$H NMR (600 MHz, D$_2$O) δ7.50 (s, 1H), 6.83-6.90 (m, 4H), 6.71 (dd, J=8.1, 1.9 Hz, 1H), 6.63-6.68 (m, 3H), 6.46 (d, J=1.9 Hz, 1H), 6.29 (ddd, J=9.1, 9.1, 2.1 Hz, 2H), 5.06 (dd, J=9.5, 3.7 Hz, 1H), 4.99 (dd, J=10.3, 3.4 Hz, 1H), 4.39 (d, J=1.0 Hz, 1H), 4.29 (d, J=1.0 Hz, 1H), 3.14 (dd, J=14.3, 3.8 Hz, 1H), 2.95-3.00 (m, 2H), 2.69 (dd, J=14.7, 10.6 Hz, 1H); $^{13}$C NMR (150 MHz, D$_2$O) δ 176.3, 173.2, 167.8, 162.9, 147.9, 143.9, 143.7, 143.4, 142.8, 142.5, 142.5, 142.2, 139.1, 132.2, 129.9, 129.3, 125.1, 124.6, 122.8, 121.7, 120.6, 119.2, 119.1, 117.3, 117.0, 116.1, 116.0, 116.0, 115.4, 115.0, 114.6, 76.1, 75.7, 45.8, 39.2, 36.7, 36.1. HRMS calculated for C$_{36}$H$_{34}$NO$_{16}$ [M+NH$_4$]$^+$: 736.1878, found: 736.1933.

Example 7

Rosmarinic Acid Purification

According to implementations, Frac#10 dry powder was reconstituted in 50% acetonitrile water mixture with 0.1% trifluoroacetic acid. The established HPLC system was described as above. In the RPC$_{18}$-HPLC experiments, Frac#10 was monitored at 214 nm. A linear gradient from 90% solvent A (98% water, 2% acetonitrile, and 0.1% trifluoroacetic acid) to 20% solvent B (90% acetonitrile, 10% water, and 0.1% trifluoroacetic acid) in 30 min was used to purify rosmarinic acid. The column was re-equilibrated with 90% solvent A for 20 min prior to each injection. Peaks were further collected by a model CHF122SB Advantec fraction collector. Rosmarinic acid was found in the peak with $T_R$=17.5 min as a single compound identified by mass spectrometry. The structure of rosmarinic acid was identified by MASS, NMR. 1 g *Plectranthus Amboinicus* dry powder can yields 8.9 mg rosmarinic acid.

(4)

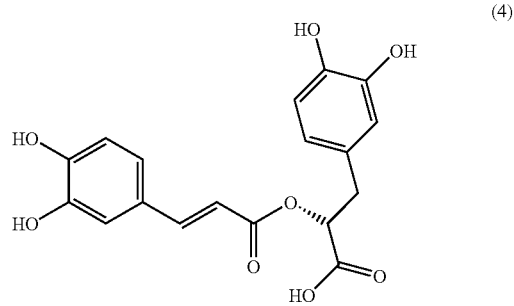

Example 8

Synthesis of Compound 7

Figure 10:
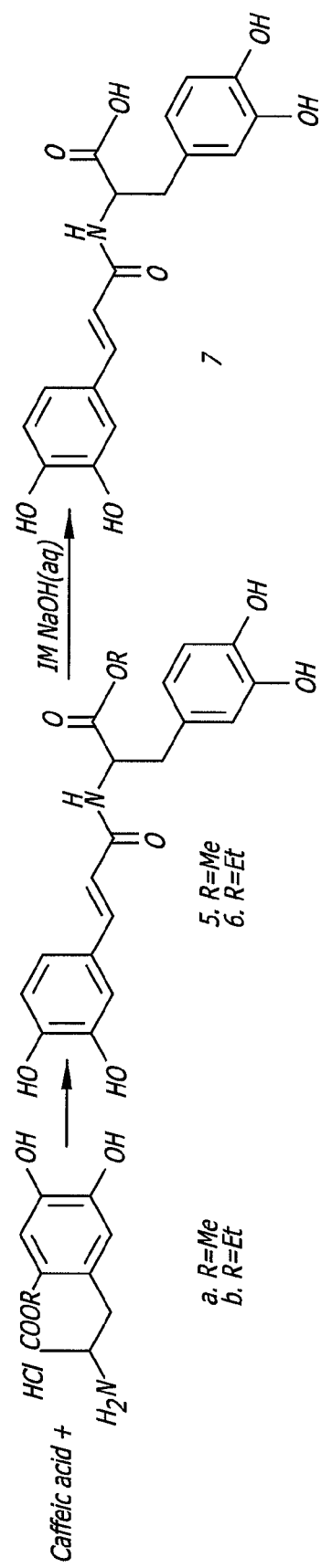
FIG. 10 is a scheme of an implementation of the synthesis of a compound of the present disclosure.

According to implementations and as illustrated by the scheme in FIG. 10, compound 7 is produced. To a solution of caffeic acid (0.25 g, 1.39 mmole) and levodopa-COOCH₃.HCl (0.55 g, 2.22 mmole) dissolved in 8.0 ml of dry DMF was added HBTU (0.63 g, 1.67 mmole) and diisopropylethylamine (2.4 ml, 13.9 mmole) and then the resulting reaction mixture was stirred at room temperature for overnight. DMF was removed in vacuo, the residue was acidified with 1 N HCl and then extracted with ethyl acetate for 4 times. Organic layer was collected, dried with MgSO$_{4(s)}$ and concentrated to give crude product. Compound 5 was obtained by column chromatography using gradient elution of ethyl acetate and hexane (0.43 g, 82% yield).

(5)

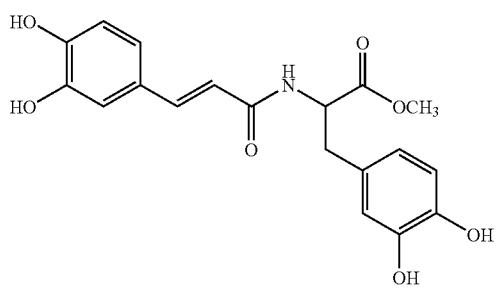

¹H-NMR (600 MHz, MeOD): δ 2.82-2.87 (m, 1H), 2.95-2.98 (m, 1H), 3.65 (s, 3H), 4.64 (dd, J=6.12, 7.98 Hz, 1H), 6.36 (d, J=15.7 Hz, 1H), 6.47 (dd, J=1.92, 8.1 Hz, 1H), 6.59 (d, J=1.92 Hz, 1H), 6.62 (d, J=8.1 Hz, 1H), 6.71 (d, J=8.04 Hz, 1H), 6.85 (dd, J=1.92, 8.16 Hz, 1H), 6.95 (d, J=1.92 Hz, 1H), 7.32 (d, J=15.7 Hz, 1H).

(6)

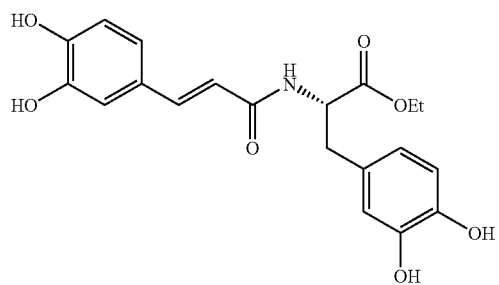

¹H-NMR (600 MHz, MeOD): δ 1.45 (t, J=6.5 Hz, 3H), 2.78-2.82 (m, 1H), 2.89-2.92 (m, 1H), 4.15 (q, J=6.5 Hz, 2H), 4.68 (dd, J=6.12, 7.98 Hz, 1H), 6.25 (d, J=15.7 Hz, 1H), 6.41 (dd, J=1.92, 8.1 Hz, 1H), 6.55 (d, J=1.92 Hz, 1H), 6.59 (d, J=8.1 Hz, 1H), 6.73 (d, J=8.04 Hz, 1H), 6.82 (dd, J=1.92, 8.16 Hz, 1H), 6.97 (d, J=1.92 Hz, 1H), 7.34 (d, J=15.7 Hz, 1H). Compound 6 was produced with 84% yield.

(7)

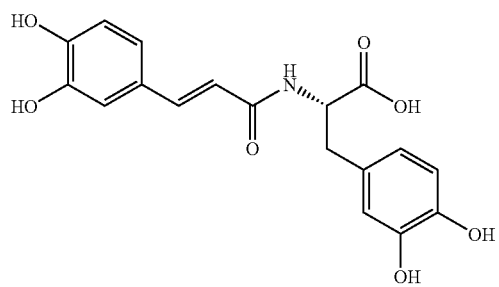

Referring again to FIG. 10, to a solution of compound 5 (0.993 g, 2.66 mmole) in 30 ml of 1,4-dioxane was added 15 ml of 1 N NaOH$_{(aq)}$. The resulting solution was stirred at room temperature and monitored by TLC plate. 6 N HCl$_{(aq)}$ was added to acidify the solution (pH~2) and stirred at room temperature for 1 hr. 1,4-Dioxane was removed under reduced pressure and aqueous layer was extracted with ethyl acetate for 4 times. The combined organic layers were dried with MgSO$_{4(s)}$ and concentrated to give crude product. Compound 7 was obtained after purification by column chromatography using gradient elution of ethyl acetate/hexane and then ethyl acetate/methanol (20% yield); ¹H-NMR (600 MHz, MeOD): δ 2.82-2.85 (m, 1H), 3.00-3.04 (m, 1H), 4.63 (dd, J=5.28, 8.16 Hz, 1H), 6.35 (d, J=15.6 Hz, 1H), 6.50 (dd, J=1.98, 8.1 Hz, 1H), 6.60 (s, 1H), 6.62 (t, J=2.04 Hz, 1H), 6.69 (d, J=8.16 Hz, 1H), 6.84 (dd, J=1.98, 8.22 Hz, 1H), 6.93 (d, J=1.98 Hz, 1H), 7.30 (d, J=15.7 Hz, 1H).

Example 9

Synthesis of Compounds 8 and 9

According to implementations, synthesis of compounds 8 and 9 are identical to that of compound 5, except by using dopamine hydrochloride (for compound 8) and diethyl 1-amino-2-(3,4-dihydroxyphenyl)ethylphosphonate (for compound 9) for the amide bond formation reaction.

(8)

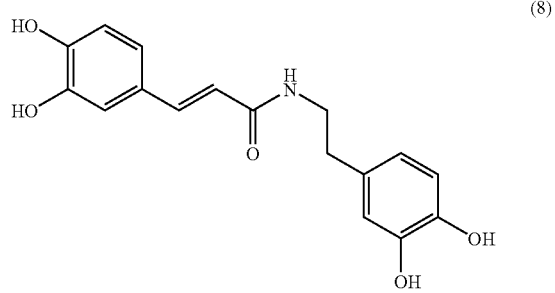

HRMS calculated for C$_{17}$H$_{18}$NO$_5$ [M+H]⁺: 316.3285, found: 316.3288. Compound 8 was synthesized with 86% yield.

(9)

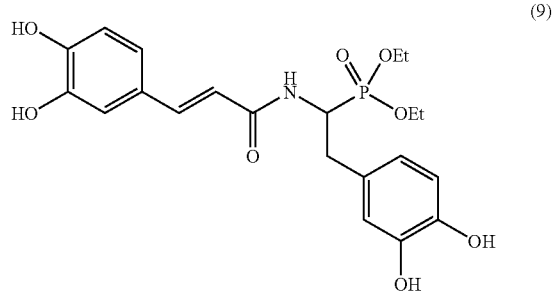

HRMS calculated for C$_{21}$H$_{27}$NO$_8$P [M+H]⁺: 452.4147, found: 452.4143. Compound 9 was synthesized with 65% yield.

Example 10

Synthesis of Compounds 11 and 12

Figure 11:
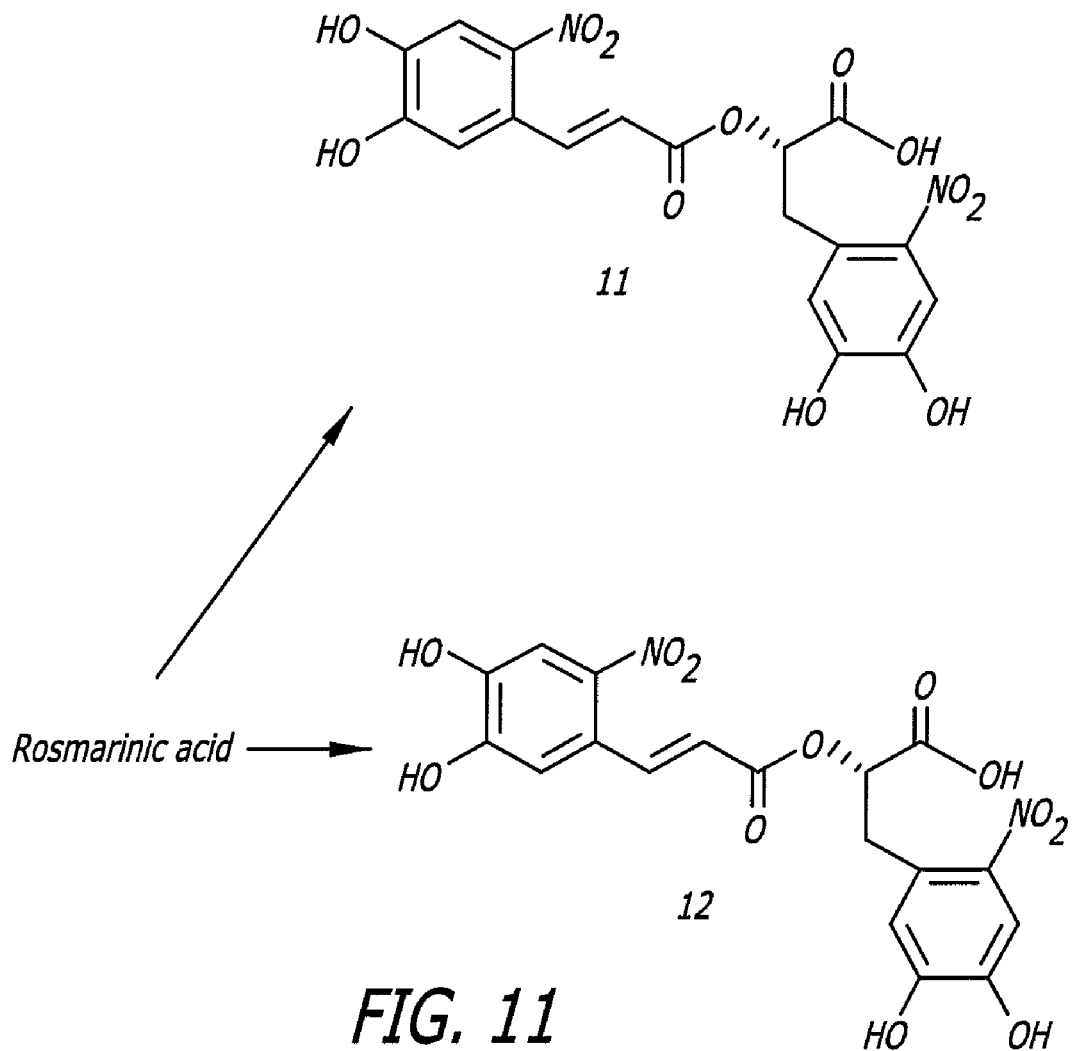
FIG. 11 is a scheme of an implementation of the synthesis of a compound of the present disclosure.

According implementations of the scheme shown in FIG. 11, compounds 11 and 12 are synthesized from rosmarinic acid. To a solution of sodium nitrite (544 mg, 7.9 mmole) in 50 ml of acetate buffer (0.2 M AcOH/0.2 M AcONa) was added rosmarinic acid (360 mg, 1.0 mmole). After 5 min (12) or 10 min (11) the solution was quenched by adding saturated sodium chloride and extracted with ethyl acetate for 5 times. The combined organic layers were dried with $NaSO_{4(s)}$ and concentrated in vacuo.

The crude product was purified by column chromatography using gradient elution of ethyl acetate/hexane and then ethyl acetate/methanol to give compound 12 (325 mg, 80% yield) and compound 11; (12) $^1$H-NMR (500 MHz, MeOD): δ 3.15-3.22 (m, 1H), 3.47-3.53 (m, 1H), 5.17 (dd, J=5.75, 11.05 Hz, 1H), 6.04 (d, J=19.89 Hz, 1H), 6.60-6.65 (m, 2H), 6.79 (dd, J=2.36, 10.25 Hz, 1H), 6.88-6.90 (m, 1H), 7.35 (d, J=19.89 Hz, 1H), 7.38 (s, 1H); (11) $^1$H-NMR (500 MHz, MeOD): δ 3.31-3.36 (m, 1H), 3.64-3.69 (m, 1H), 5.37 (dd, J=5.94, 10.9 Hz, 1H), 6.26 (d, J=19.7 Hz, 1H), 6.81 (s, 1H), 7.05 (s, 1H), 7.54 (s, 2H), 8.12 (d, J=19.7 Hz, 1H).

Example 11

Synthesis of Compounds 13

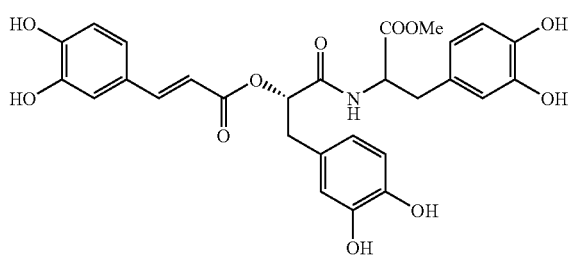

(13)

Figure 12:
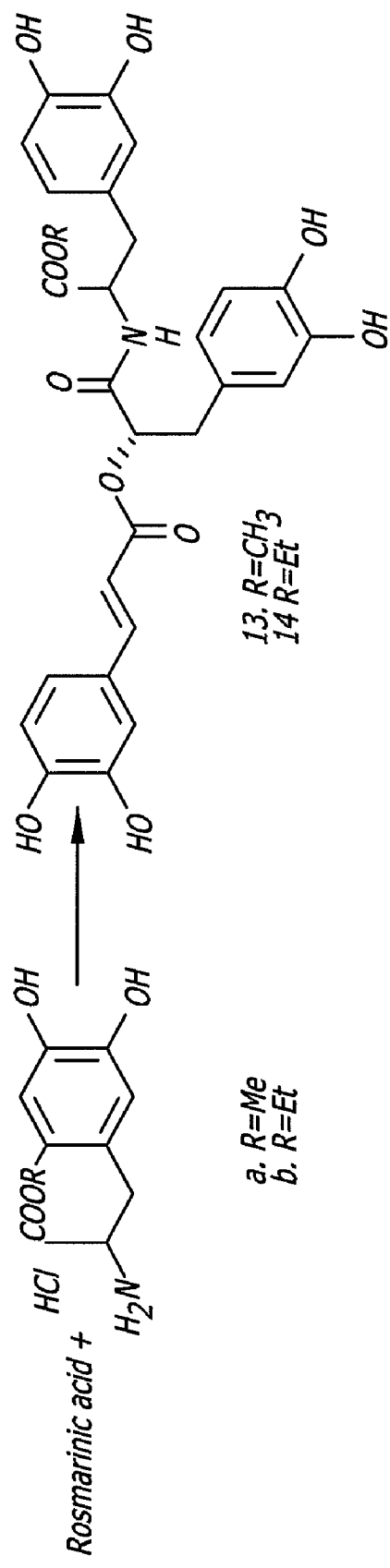
FIG. 12 is a scheme of an implementation of the synthesis of a compound of the present disclosure.

According to implementations of a scheme shown in FIG. 12, compound 13 is produced. To a solution of rosmarinic acid (0.5 g, 1.39 mmole) and levodopa-COOCH$_3$.HCl (0.55 g, 2.22 mmole) dissolved in 8.0 ml of dry DMF was added HBTU (0.63 g, 1.67 mmole) and diisopropylethylamine (2.4 ml, 13.9 mmole) and then the resulting reaction mixture was stirred at room temperature for overnight. DMF was removed in vacuo, the residue was acidified with 1 N HCl and then extracted with ethyl acetate for 4 times. Organic layer was collected, dried with $MgSO_{4(s)}$ and concentrated to give crude product.

Compound 13 was obtained by column chromatography using gradient elution of ethyl acetate and hexane (0.26 g, 34% yield); $^1$H-NMR (600 MHz, MeOD): δ 2.74-2.90 (m, 4H), 3.64 (s, 3H), 4.54 (dd, J=6.0, 7.8 Hz, 1H), 5.16 (dd, J=4.98, 7.8 Hz, 1H), 6.21 (d, J=15.8 Hz, 1H), 6.35 (dd, J=1.92, 8.04 Hz, 1H), 6.47 (dd, J=1.92, 8.1 Hz, 1H), 6.52 (d, J=1.92 Hz, 1H), 6.56 (d, J=7.98 Hz, 1H), 6.61-6.63 (m, 2H), 6.73 (d, J=8.16 Hz, 1H), 6.91 (dd, J=1.92, 8.22 Hz, 1H), 7.00 (d, J=1.92 Hz, 1H), 7.49 (d, J=15.8 Hz, 1H).

Example 11

Synthesis of Compounds 14

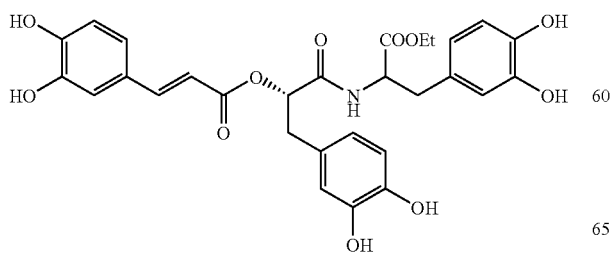

(14)

According to implementations of a scheme shown in FIG. 12, compound 13 is produced. The procedure is disclosed in Example 11. Compound 14 is produced in 38% yield.

$^1$H-NMR (600 MHz, MeOD): δ 1.56 (t, J=6.6 Hz, 3H), 2.76-2.88 (m, 4H), 4.23 (q, J=6.6 Hz, 2H), 4.46 (dd, J=6.0, 7.8 Hz, 1H), 5.02 (dd, J=4.98, 7.8 Hz, 1H), 6.33 (d, J=15.8 Hz, 1H), 6.38 (dd, J=1.92, 8.04 Hz, 1H), 6.50 (dd, J=1.92, 8.1 Hz, 1H), 6.56 (d, J=1.92 Hz, 1H), 6.61 (d, J=7.98 Hz, 1H), 6.67-6.69 (m, 2H), 6.74 (d, J=8.16 Hz, 1H), 6.87 (dd, J=1.92, 8.22 Hz, 1H), 7.02 (d, J=1.92 Hz, 1H), 7.54 (d, J=15.8 Hz, 1H).

Example 12

Synthesis of Compounds 15 and 15'

Figure 13:
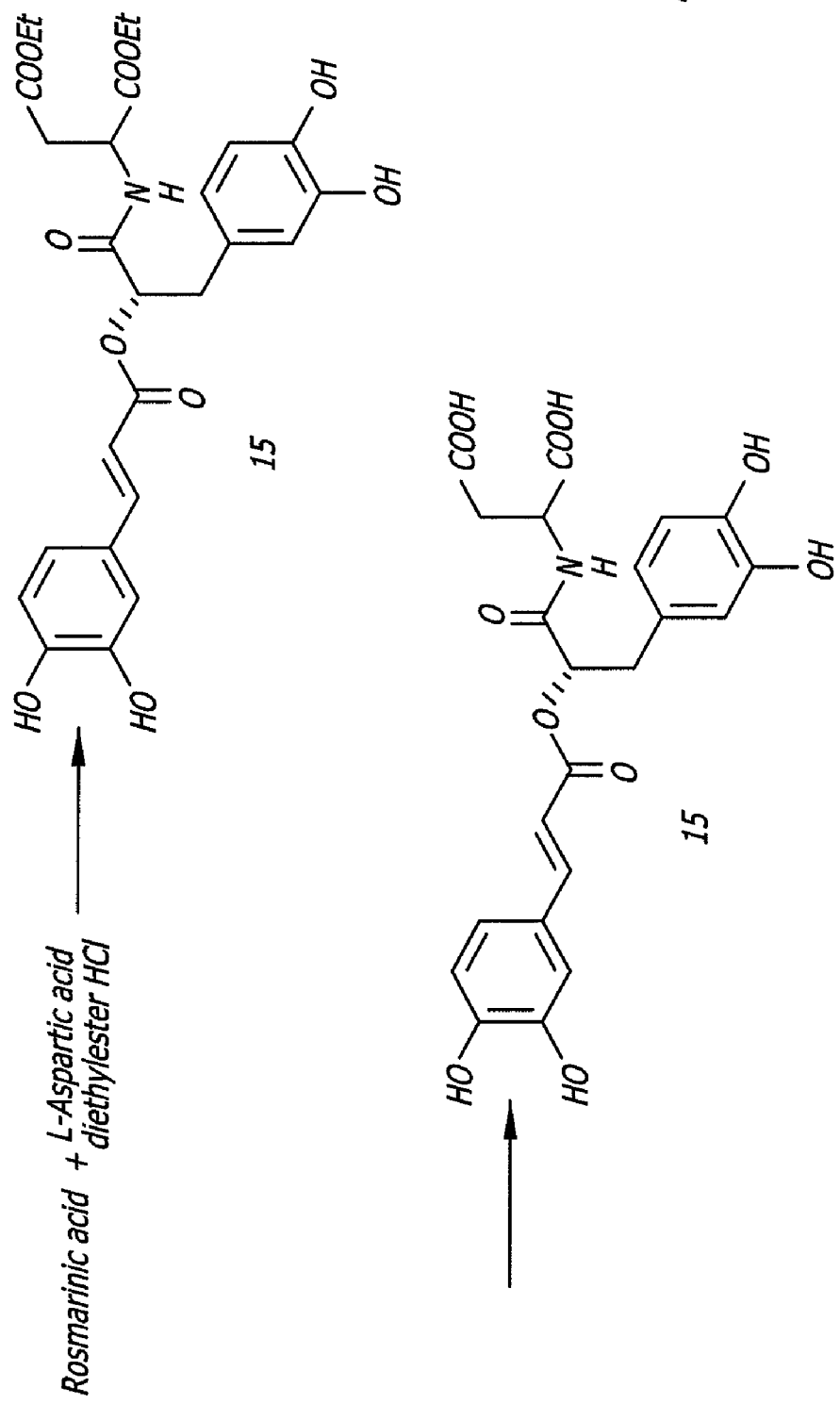
FIG. 13 is a scheme of an implementation of the synthesis of a compound of the present disclosure.

According to implementations and the scheme shown in FIG. 13, compound 15 is synthesized. rosmarinic acid was treated by the same procedure described for compound 13 except using L-Aspartic acid diethyl ester.HCl to produce compound 15' (27% yield); $^1$H-NMR (600 MHz, MeOD): δ 1.16-1.21 (m, 6H), 2.67-2.77 (m, 2H), 2.91-2.99 (m, 2H), 4.04 (dd, J=7.08, 14.04 Hz, 4.12 (dd, J=7.14, 14.28 Hz, 2H), 4.70 (t, J=6.06 Hz, 1H), 5.21 (dd, J=5.52, 7.56 Hz, 1H), 6.23 (d, J=15.9 Hz, 1H), 6.52 (dd, J=1.92, 8.04 Hz, 1H), 6.62 (d, J=8.04 Hz, 1H), 6.65 (d, J=1.92 Hz, 1H), 6.73 (d, J=8.16 Hz, 1H), 6.91 (dd, J=1.98, 8.16 Hz, 1H), 6.99 (d, J=1.92 Hz, 1H), 7.52 (d, J=15.9 Hz, 1H)

Compound 15' (100 mg, 0.19 mmole) was dissolved in 4.0 ml of co-solvent (1:1) of acetonitrile and water. LiOH (46 mg, 1.9 mmole) was added into the solution at 0° C. and then the whole solution was stirred at 0° C. and monitored by TLC plate. The solution was acidified with 6 N. $HCl_{(aq)}$ to pH=2 and stirred at 0° C. for 30 min. Aqueous layer was extracted with ethyl acetate for 4 times and organic layer was collected, dried with $MgSO_{4(s)}$ and concentrated to give crude product. Crude product was purified on silica gel using gradient elution of ethyl acetate/hexane followed by ethyl acetate/methanol to furnish compound 15 (40 mg, 44% yield); $^1$H-NMR (600 MHz, MeOD): δ 2.73 (d, J=5.7 Hz, 2H), 2.91-3.01 (m, 2H), 4.65 (t, J=5.58 Hz, 1H), 5.24 (dd, J=4.8, 8.22 Hz, 1H), 6.22 (d, J=15.9 Hz, 1H), 6.52 (dd, J=1.68, 7.98 Hz, 1H), 6.61 (d, J=8.1 Hz, 1H), 6.65 (d, J=1.68 Hz, 1H), 6.72 (d, J=8.16 Hz, 1H), 6.90 (dd, J=1.8, 8.16 Hz, 1H), 6.99 (d, J=1.8 Hz, 1H), 7.50 (d, J=15.84 Hz, 1H).

Example 13

Synthesis of Compound 16

Figure 14:
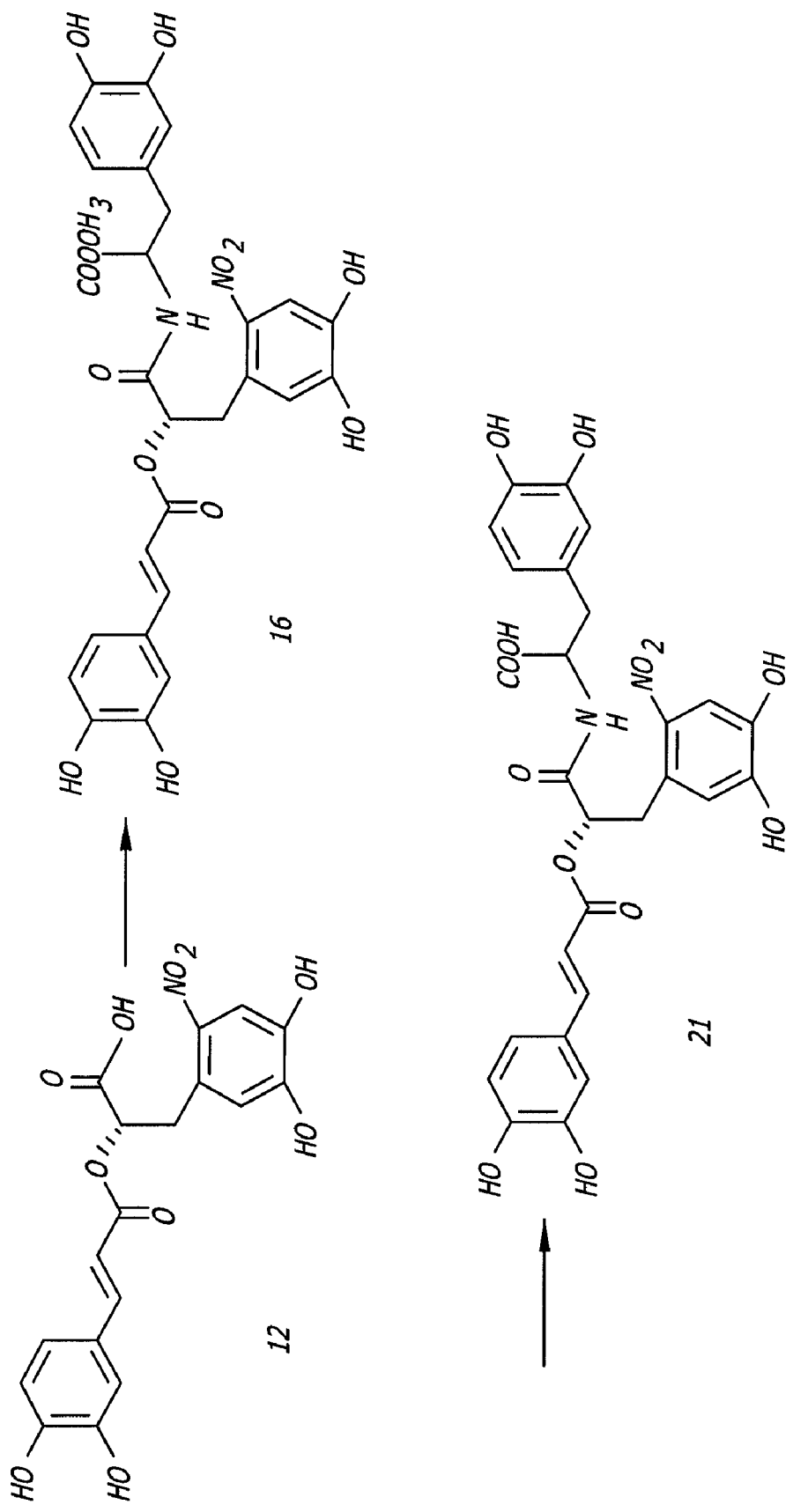
FIG. 14 is a scheme of an implementation of the synthesis of a compound of the present disclosure.

According to implementations and as illustrated by the scheme in FIG. 14, levodopa-COOCH$_3$.HCl was treated by the same procedure described for compound 13 except using compound 12 to produce compound 16. $^1$H-NMR (500 MHz, MeOD): δ 2.73-2.83 (m, 4H), 3.60 (s, 3H), 4.47-4.49 (m, 1H), 5.26 (dd, J=4.69, 8.53 Hz, 1H), 6.09 (d, J=15.8 Hz, 1H), 6.32 (dd, J=2.06, 8.03 Hz, 1H), 6.47 (d, J=2.02 Hz, 1H), 6.50 (d, J=8.0 Hz, 1H), 6.63 (s, 1H), 6.68 (d, J=8.15 Hz, 1H), 6.86 (dd, J=2.02, 8.23 Hz, 1H), 6.95 (d, J=2.01 Hz, 1H), 7.00-7.04 (m, 1H), 7.13-7.16 (m, 1H).

Example 14

Synthesis of Compound 21

Referring again to implementations of the present disclosure shown in the scheme in FIG. 14, compound 16 was treated by the same procedure described for compound 15 to give compound 21. According to implementations, compound 21 was recovered with a 52% yield. HRMS calculated for $C_{27}H_{23}N_2O_{13}$ [M–H]$^-$: 583.4771, found: 583.4768.

Example 15

Synthesis of Compound 17

Figure 15:
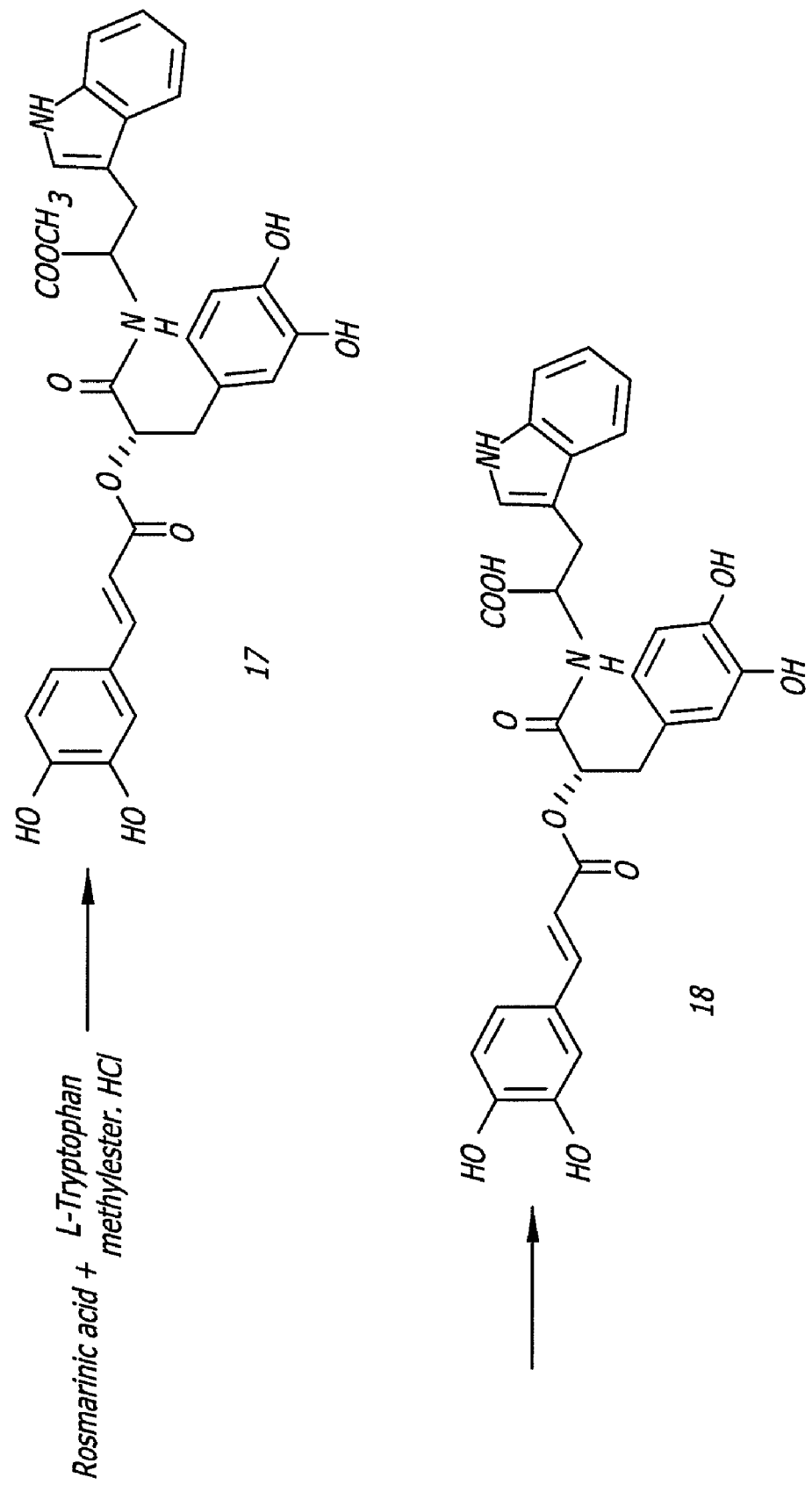
FIG. 15 is a scheme of an implementation of the synthesis of a compound of the present disclosure.

According to implementations and as shown by the scheme in FIG. 15, compound 17 is synthesized. rosmarinic acid was treated by the same procedure described for compound 13 except using L-Tryptophan methyl ester.HCl to produce compound 17 (43% yield); $^1$H-NMR (500 MHz, MeOD): δ 2.82-2.89 (m, 2H), 3.12-3.24 (m, 2H), 3.61 (s, 3H), 4.73 (dd, J=5.92, 7.18 Hz, 1H), 5.24 (dd, J=5.39, 7.37 Hz, 1H), 6.14 (d, J=15.9 Hz, 1H), 6.46 (dd, J=1.88, 8.06 Hz, 1H), 6.63 (d, J=8.04 Hz, 1H), 6.66 (d, J=1.86 Hz, 1H), 6.76 (d, J=8.18 Hz, 1H), 6.88-6.96 (m, 3H), 7.01 (dd, J=6.62, 8.15 Hz, 2H), 7.25 (d, J=8.09 Hz, 1H), 7.43 (d, J=7.88 Hz, 1H), 7.47 (d, J=15.9 Hz, 1H).

Example 16

Synthesis of Compound 18

According to implementations and as shown by the scheme in FIG. 15, compound 17 was treated by the same procedure described for compound 15 to furnish compound 18 (45% yield); $^1$H-NMR (600 MHz, MeOD): δ 2.75-2.83 (m, 2H), 3.09-3.25 (m, 2H), 4.48 (s, 1H), 5.14 (s, 1H), 5.96 (d, J=15.84 Hz, 1H), 6.36 (d, J=7.98 Hz, 1H), 6.50 (d, J=8.04 Hz, 1H), 6.53 (s, 1H), 6.66 (d, J=7.92 Hz, 1H), 6.78-6.88 (m, 5H), 7.06 (d, J=7.98 Hz, 1H), 7.29 (d, J=15.96 Hz, 1H), 7.40 (d, J=7.86 Hz, 1H).

Example 17

Synthesis of Compound 19

Figure 16:
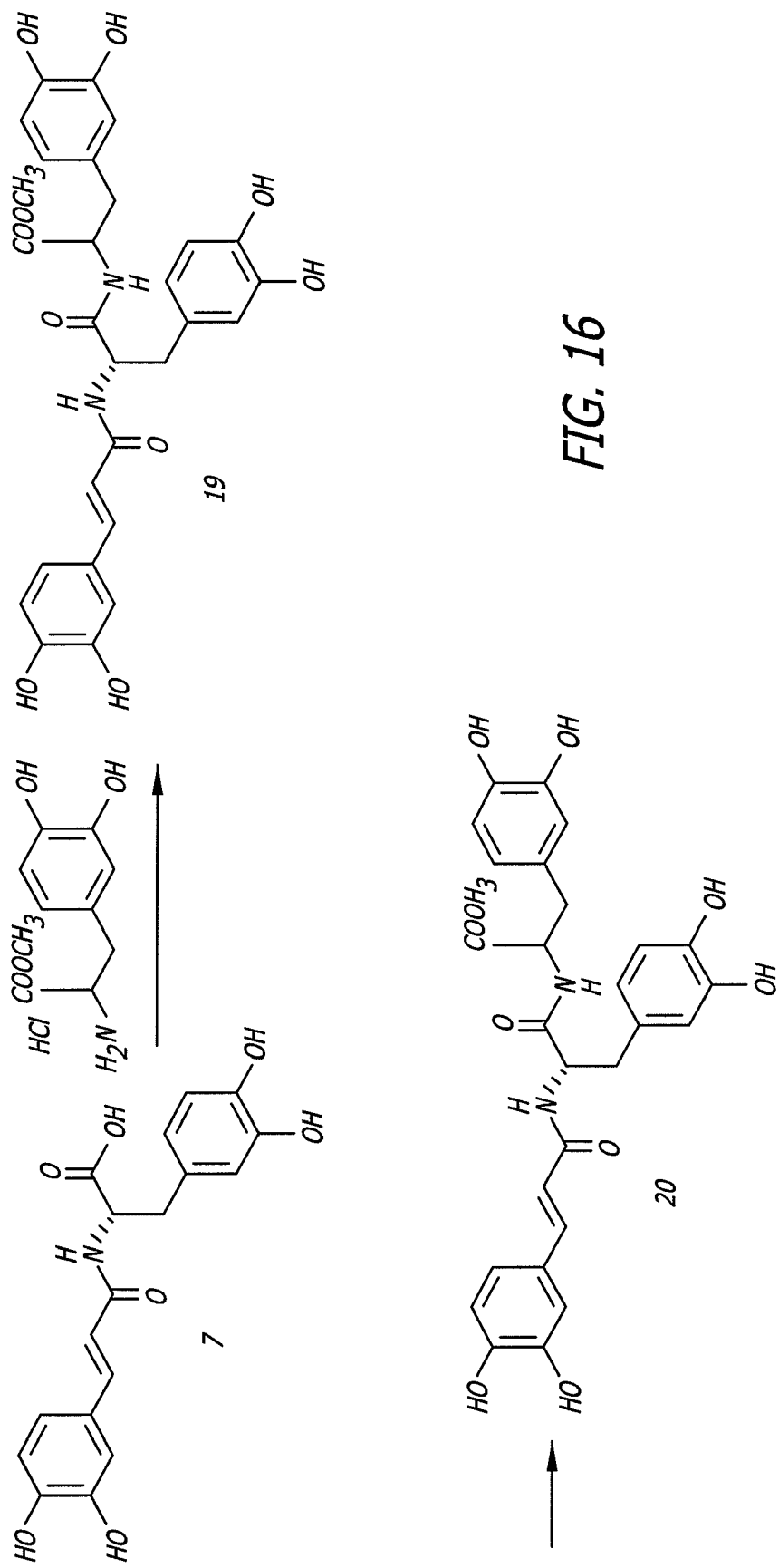
FIG. 16 is scheme of an implementation of the synthesis of a compound of the present disclosure.

According to implementations and as shown by the scheme in FIG. 16, levodopa-COOCH$_3$.HCl was treated by the same procedure described for compound 7 to afford compound 19 (70% yield); $^1$H-NMR (600 MHz, MeOD): δ 2.73-2.94 (m, 4H), 3.6 (s, 3H), 4.52 J=6.7 Hz, 1H), 4.59 (dd, J=6.5 Hz, 1H), 6.33 (d, J=15.7 Hz, 1H), 6.35 (d, J=2.04 Hz, 1H), 6.39-6.42 (m, 1H), 6.49 (d, J=2.1 Hz, 1H), 6.51 (dd, J=1.98, 13.62 Hz, 1H), 6.56-6.62 (m, 4H), 6.70 (d, J=8.16 Hz, 1H), 6.84-6.89 (m, 1H), 6.95 (d, J=1.98 Hz, 1H), 7.31 (d, J=15.7 Hz, 1H).

Example 18

Synthesis of Compound 20

According to implementations and as shown by the scheme in FIG. 16, compound 19 was treated by the same procedure described for compound 7 to give compound 20 (44% yield); $^1$H-NMR (600 MHz, MeOD): δ 2.62-2.71 (m, 1H), 2.76-2.91 (m, 2H), 2.95-2.99 (m, 1H), 4.51 (dd, J=5.76, 12.6 Hz, 1H), 4.61 (m, 1H), 6.31 (d, J=15.7 Hz, 1H), 6.37 (d, J=8.04 Hz, 1H), 6.45 (dd, J=1.86, 8.04 Hz, 1H), 6.50 (dd, J=1.8, 8.04 Hz, 1H), 6.57-6.63 (m, 4H), 6.70 (J=8.16 Hz, 1H), 6.85 (dd, J=1.86, 8.28 Hz, 1H), 6.94 (d, J=1.8 Hz, 1H), 7.29 (d, =15.7 Hz, 1H).

Example 19

Materials and Methods—Isolation and Purification of Mena 987/998/9102 and Rosmarinic Acid from *Plectranthus amboinicus*

Materials

*Plectranthus amboinicus* leaves (batch #9) were washed with double deionized H$_2$O thoroughly and air dried briefly to remove water residuals before homogenized. The crude leaf juice was centrifuged with a model Beckman centrifugator at 10,000×g for 30 min at 4° C. The clear supernatant recovered from crude leaf juice was further filtered through No. 1 filter paper (125 mm, Advantec, lot no. 60821017) to remove the impurities and leaf debris. The filtrate was then lyophilized and the dry powder was stored at room temperature till RPC$_{18}$-HPLC fractionation. According to our estimation, 476.3 g *Plectranthus amboinicus* leaves can produce 440 ml leaf juice (7.4 g dry powder).

The Crude Sample Preparation of *Plectranthus amboinicus*

*Plectranthus amboinicus* dry powder (1 g) was dissolved possibly in 25% acetonitrile water mixture with 0.1% trifluoroacetic acid. Samples were centrifuged at 14,000×rpm for 1 min at room temperature with a desktop centrifuge before each injection.

RPC$_{18}$-HPLC Purification

The HPLC purification was performed on an Agilent Technologies 1200 system, equipped with a 4-channel programmable pumps and a model G13658 UV/VIS detector. In the RPC$_{18}$-HPLC experiments, all the samples were monitored at 214 nm. These samples were initially separated on a Discovery BIO Wide Pore C$_{18}$ reversed-phase column (5 μm, 25 cm×10 mm, Supelco) at a flow rate of 2.5 ml/min with an injection volume of 100 μl. A linear gradient from solvent A (98% water, 2% acetonitrile, and 0.1% trifluoroacetic acid) to solvent B (90% acetonitrile, 10% water, and 0.1% trifluoroacetic acid) in 60 min was used for separation. The column was re-equilibrated with 100% solvent A for 20 min prior to each injection. The products purified by RPC$_{18}$-HPLC were lyophilized to remove the mobile phase and then stored at room temperature before further separation. According to the elution profile, 3 fractions were collected by a model CHF122SB Advantec fraction collector. Frac#8 was collected from 19.5 to 21.5 min, Frac#9 was collected from 21.5 to 23.5 min and Frac#10 was collected from 23.5 to 25.5 min. Generally, 1 g *Plectranthus amboinicus* dry powder can yields 4.8 mg Frac#8, 14 mg Frac#9 and 12.7 mg Frac#10.

While the compositions and methods have been described in terms of what are presently considered to be the most practical and preferred implementations, it is to be understood that the disclosure need not be limited to the disclosed implementations. It is intended to cover various modifications and similar arrangements included within the spirit and scope of the claims, the scope of which should be accorded the broadest interpretation so as to encompass all such modifications and similar structures. The present disclosure includes any and all implementations of the following claims.

The invention claimed is:
1. A purified compound having the formula:
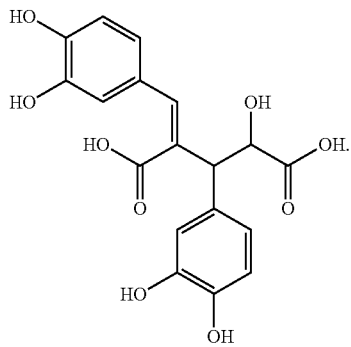
2. A pharmaceutical composition comprising: a pharmaceutically acceptable carrier and a purified compound having the formula:
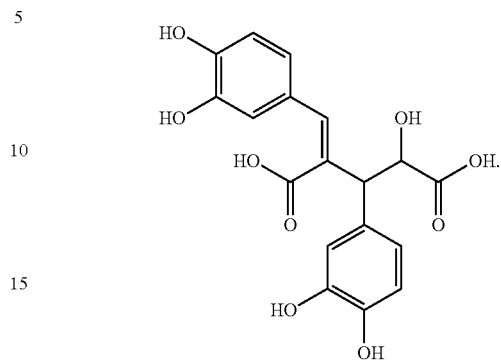
* * * * *